US008885155B2

(12) United States Patent
Li et al.

(10) Patent No.: US 8,885,155 B2
(45) Date of Patent: Nov. 11, 2014

(54) COMBINED LIGHT SOURCE PHOTOACOUSTIC SYSTEM

(75) Inventors: Youzhi Li, Longmont, CO (US); Bo Chen, Louisville, CO (US)

(73) Assignee: Covidien LP, Mansfield, MA (US)

( * ) Notice: Subject to any disclaimer, the term of this patent is extended or adjusted under 35 U.S.C. 154(b) by 117 days.

(21) Appl. No.: 13/459,933

(22) Filed: Apr. 30, 2012

(65) Prior Publication Data
US 2013/0286379 A1    Oct. 31, 2013

(51) Int. Cl.
*G01N 33/48*    (2006.01)
*G01N 21/00*    (2006.01)

(52) U.S. Cl.
USPC .............................................. 356/40; 356/436

(58) Field of Classification Search
USPC .............. 356/39–42, 432, 436; 600/310–344; 604/20–21
See application file for complete search history.

(56) References Cited

U.S. PATENT DOCUMENTS

| | | | |
|---|---|---|---|
| 4,385,634 A | 5/1983 | Bowen | |
| 5,348,002 A | 9/1994 | Caro | |
| 5,657,754 A | 8/1997 | Rosencwaig | |
| 5,840,023 A | 11/1998 | Oraevsky et al. | |
| 5,941,821 A | 8/1999 | Chou | |
| 6,049,728 A | 4/2000 | Chou | |
| 6,104,942 A | 8/2000 | Kruger | |
| 6,309,352 B1 | 10/2001 | Oraevsky et al. | |
| 6,393,315 B1 * | 5/2002 | Aprahamian et al. | ........ 600/476 |
| 6,403,944 B1 | 6/2002 | MacKenzie et al. | |
| 6,405,069 B1 | 6/2002 | Oraevsky et al. | |
| 6,466,806 B1 | 10/2002 | Geva et al. | |
| 6,484,044 B1 | 11/2002 | Lilienfeld-Toal | |
| 6,498,942 B1 | 12/2002 | Esenaliev et al. | |
| 6,751,490 B2 | 6/2004 | Esenaliev et al. | |
| 6,839,496 B1 | 1/2005 | Mills et al. | |
| 6,846,288 B2 | 1/2005 | Nagar et al. | |
| 7,322,972 B2 | 1/2008 | Viator et al. | |
| 7,430,445 B2 | 9/2008 | Esenaliev et al. | |
| 7,515,948 B1 | 4/2009 | Balberg et al. | |

(Continued)

FOREIGN PATENT DOCUMENTS

| | | |
|---|---|---|
| EP | 0282234 | 9/1988 |
| JP | 2007259918 | 10/2007 |
| WO | 2007100937 A2 | 9/2007 |

OTHER PUBLICATIONS

Brecht, Hans-Peter, "Noninvasive Optoacoustic Monitoring of Blood Oxygenation in Large Blood Vessels," Thesis, The University of Texas Medical Branch, Dec. 2007, pp. i-xviii; 1-131.

(Continued)

*Primary Examiner* — Kara E Geisel
*Assistant Examiner* — Dominic J Bologna
(74) *Attorney, Agent, or Firm* — Fletcher Yoder PC

(57) ABSTRACT

A physiological monitoring system may use photoacoustic sensing to determine one or more physiological parameters of a subject. The photoacoustic system may use two light sources (e.g., a high power pulsed laser diode and a continuous wave laser diode) to generate acoustic pressure signals in a subject. One or more light sources (e.g., the high powered pulsed laser diode) may provide a high signal-to-noise ratio. The high signal-to-noise ratio signals may provide high sensitivity for physiological measurements (e.g., cardiac output and temperature measurements). The photoacoustic system may use high powered light sources in combination with other light sources to improve physiological measurements.

23 Claims, 9 Drawing Sheets

(56) References Cited

U.S. PATENT DOCUMENTS

| | | | |
|---|---|---|---|
| 7,729,734 | B2 | 6/2010 | Mandelis et al. |
| 2005/0070803 | A1 | 3/2005 | Cullum et al. |
| 2006/0184042 | A1 | 8/2006 | Wang et al. |
| 2006/0272418 | A1 | 12/2006 | Maris et al. |
| 2007/0197886 | A1 | 8/2007 | Naganuma et al. |
| 2008/0255433 | A1* | 10/2008 | Prough et al. ............ 600/301 |
| 2009/0149761 | A1* | 6/2009 | Zou et al. ................ 600/476 |
| 2009/0171172 | A1* | 7/2009 | Bordon et al. ........... 600/324 |
| 2010/0285518 | A1* | 11/2010 | Viator et al. ............. 435/29 |
| 2010/0292547 | A1 | 11/2010 | Mandelis et al. |
| 2011/0201914 | A1 | 8/2011 | Wang et al. |
| 2011/0275890 | A1 | 11/2011 | Wang et al. |
| 2012/0022338 | A1* | 1/2012 | Subramaniam et al. ...... 600/301 |
| 2012/0029829 | A1 | 2/2012 | Li et al. |
| 2013/0102865 | A1* | 4/2013 | Mandelis et al. ......... 600/328 |

OTHER PUBLICATIONS

Esenaliev, Rinat O., et al., "Continuous, Noninvasive Monitoring of Total Hemoglobin Concentration by an Optoacoustic Technique," Applied Optics, vol. 43, No. 17, 2007, pp. 3401-3407.

Fan, Ying, et al., "Laser Photothermoacoustic Heterodyned Lock-in Depth Profilometry in Turbid Tissue Phantoms," Phys. Rev. E, vol. 72, 2005, pp. 051908•1-051908•11.

Guo, Zijian, et al., "On the Speckle-free Nature of Photoacoustic Tomography," Med. Phys., vol. 37, No. 9, 2009, pp. 4084-4088.

Guo, Zijian, et al., "Calibration-free Absolute Quantification of Optical Absorption Coefficients Using Acoustic Spectra in 3D Photoacoustic Microscopy of Biological Tissue," Optics Letters, vol. 35, 2010, pp. 2067-2069.

Hu, Song, et al., "Noninvasive Label-free Imaging of Microhemodynamics by Optical-resolution Photoacoustic Microscopy," Optics Express, vol. 17, No. 9, 2009, pp. 7688-7693.

Larina, Irina V., et al., "Real-Time Optoacoustic Monitoring of Temperature in Tissues," J. Phys. D: Appl. Phys., vol. 38, 2005, pp. 2633-2639.

Laufer, Jan, et al., "In Vitro Measurements of Absolute Blood Oxygen Saturation Using Pulsed Near-Infrared Photoacoustic Spectroscopy: Accuracy and Resolution," Phys. Med. Biol., vol. 50, 2005, pp. 4409-4428.

Petrova, Irina Y., et al., "Clinical Tests of Highly Portable, 2-Ib, Laser Diode-based, Noninvasive, Optoacoustic Hemoglobin Monitor," Proc. of SPIE, vol. 7177, 2009, pp. 717705•1-717705•6.

Pramanik, Manojit, et al., "Thermoacoustic and Photoacoustic Sensing of Temperature," Journal of Biomedical Optics, vol. 14, No. 5, 2009, pp. 054024•1-054024•7.

Ranasinghesagara, Janaka C., et al., "Combined Photoacoustic and Oblique-incidence Diffuse Reflectance System for Quantitative Photoacoustic Imaging in Turbid Media," Journal of Biomedical Optics, vol. 15, No. 4, 2010, pp. 046016•1-046016•5.

Telenkov, Sergey A., et al., "Photothermoacoustic Imaging of Biological Tissues: Maximum Depth Characterization Comparison of Time and Frequency-domain Measurements," Journal of Biomedical Optics, vol. 14, No. 4, 2009, 044025•1-044025•12.

Meditsinskie pribory. Razrabotka i primenenie. Edited by I.V. Kamyschko, M., "Meditsinskaya kniga", 2004, p. 435-436.

International Search Report and Written Opinion for PCT/US2013/038913 dated Aug. 15, 2013; 7 pgs.

* cited by examiner

COMBINED LIGHT SOURCE PHOTOACOUSTIC SYSTEM

The present disclosure relates to a combined light source photoacoustic system, and more particularly relates to determining physiological parameters using two different light sources.

SUMMARY

Systems and methods are provided for determining physiological parameters using two light sources in a photoacoustic system. The first light source may be configured to provide a pulsed photonic signal to a subject. The second light source may be configured to provide a modulated photonic signal to the subject. In some embodiments, the first light source may be a pulsed laser diode (e.g., having an emission wavelength of 905 nm) and the second light source may be a continuous wave diode. A detector may be used to detect first and second acoustic pressure signals from the subject. The first acoustic pressure signal may be generated by the absorption of at least some of the pulsed photonic signal by the subject. The second acoustic pressure signal may be generated by the absorption of at least some of the modulated photonic signal by the subject. The acoustic pressure signals may include different components corresponding to different wavelengths and modulations of light provided by the light sources and the acoustic pressure signals may include information related to physiological parameters. One or more physiological parameters may be determined based on the acoustic pressure signals.

In some embodiments, acoustic pressure signals associated with photonic signals from pulsed laser diodes may provide a high signal to noise ratio due in part to the relatively large peak power output of pulsed laser diodes as compared to continuous wave diodes. In some embodiments, photonic signals from pulsed laser diodes may be used to determine certain physiological parameters including, for example, cardiac output and temperature. In some embodiments, the system may also use continuous wave diodes due in part to the range of availability of emission wavelengths. In some embodiments, acoustic pressure signals associated with photonic signals from continuous wave diodes may be used to determine wavelength-dependent physiological parameters including, for example, hemoglobin concentration and blood oxygen saturation. In some embodiments, a photoacoustic system may use both pulsed laser diodes and continuous wave diodes. For example, the system may concurrently use a pulsed laser diode to determine temperature and/or cardiac output and two continuous wave diodes to determine hemoglobin concentration and/or blood oxygen saturation. In another embodiment, the system may use a pulsed laser diode at a first wavelength and a continuous wave diode at a second wavelength to concurrently determine temperature and/or cardiac output and hemoglobin concentration and/or blood oxygen saturation.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
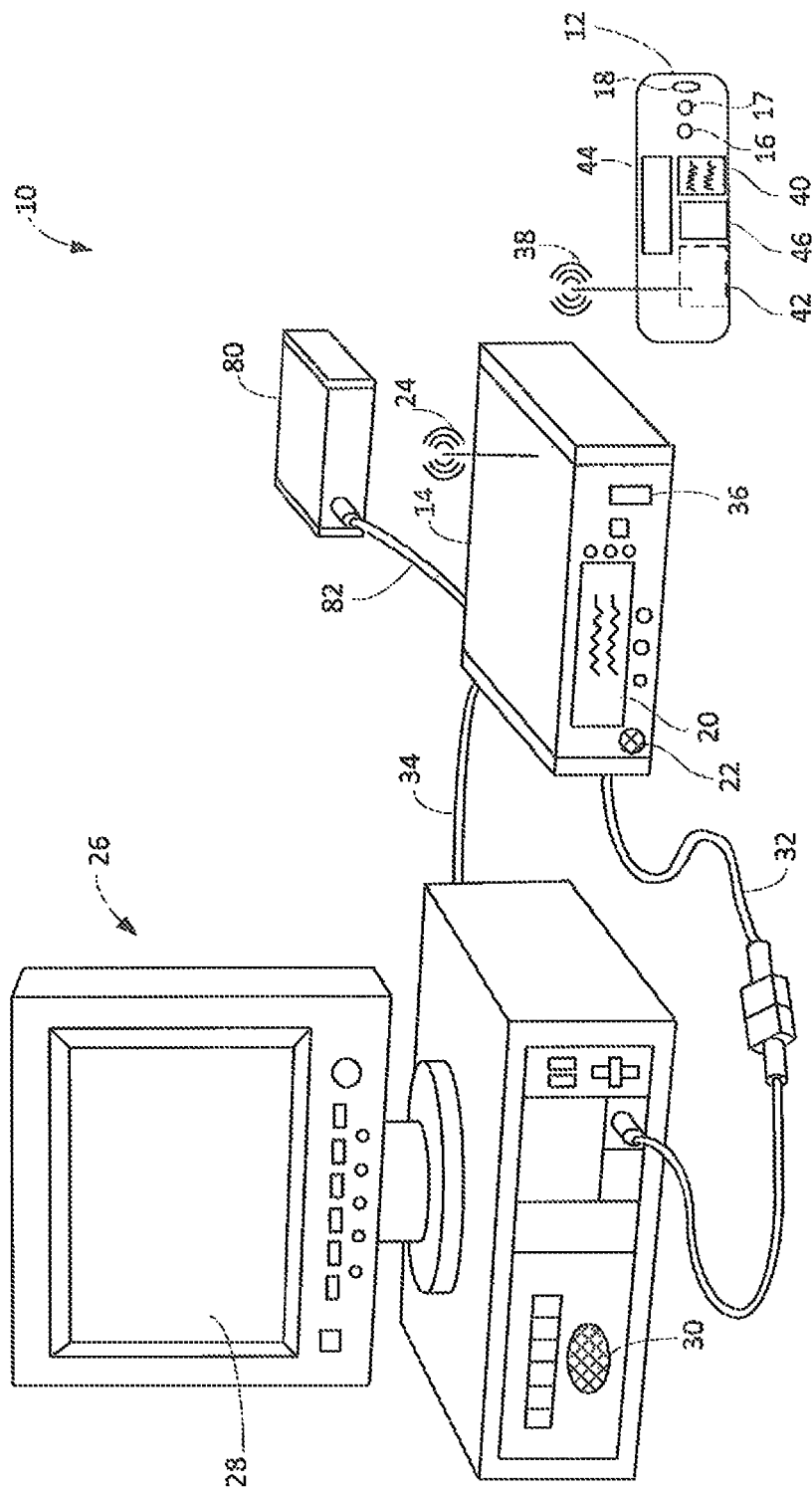
FIG. 1 shows an illustrative physiological monitoring system in accordance with some embodiments of the present disclosure.

Photoacoustics (or "optoacoustics") or "the photoacoustic effect" (or "optoacoustic effect") refers to the phenomenon in which one or more wavelengths of light are presented to and absorbed by one or more constituents of an object, thereby causing an increase in kinetic energy of the one or more constituents, which causes an associated pressure response within the object. Particular modulations or pulsing of the incident light, along with measurements of the corresponding pressure response in, for example, tissue of the subject, may be used for physiological parameter determination, medical imaging, or both. For example, the concentration of a constituent, such as hemoglobin (e.g., oxygenated, deoxygenated and/or total hemoglobin) may be determined using photoacoustic analysis. In a further example, one or more hemodynamic parameters such as cardiac output (CO), intrathoracic blood volume (ITBV), intrathoracic circulatory volume (ITCV), global end-diastolic volume (GEDV), pulmonary circulatory volume (PCV), extravascular lung water (EVLW), and/or any other suitable hemodynamic parameters may be determined using photoacoustic analysis and indicator dilution techniques. In a further example, physiological parameters such as temperature and blood pressure may be determined using photoacoustic analysis. In some embodiments, the system may use multiple wavelengths of light from multiple light sources to determine physiological parameters, for example, blood oxygen concentration. In some embodiments, the system may use a single light source to determine physiological parameters, for example, temperature or cardiac output.

A photoacoustic system may include a photoacoustic sensor that is placed at a site on a subject, typically a cheek, tongue, temple, neck, palm, fingertip, toe, forehead or earlobe, or in the case of a neonate, across a foot. In some embodiments, the photoacoustic sensor can be placed anywhere where an artery or vessel is accessible noninvasively. The photoacoustic system may use multiple light sources, and any suitable light guides (e.g., fiber optics), to pass light through the subject's tissue, or a combination of tissue thereof (e.g., organs) and one or more acoustic detectors to sense the pressure response of the tissue induced by light absorption. Tissue may include muscle, fat, blood, blood vessels, and/or any other suitable tissue types. In some embodiments, the light sources may be lasers or laser diodes operated in pulsed and continuous wave (CW) modes. In some embodiments, the acoustic detector may be an ultrasound detector, which may be suitable to detect pressure fluctuations arising from the constituent's absorption of the incident light of the light source.

In some embodiments, the light from the light sources may be focused, shaped, or otherwise spatially modulated to illuminate a particular region of interest. In some arrangements, photoacoustic monitoring may allow relatively higher spatial resolution than line of sight optical techniques (e.g., path integrated absorption measurements). The enhanced spatial resolution of the photoacoustic technique may allow for imaging, scalar field mapping, and other spatially resolved results, in 1, 2, or 3 spatial dimensions. The acoustic response to the photonic excitation may radiate from the illuminated region of interest, and accordingly may be detected at multiple positions.

The photoacoustic system may measure the pressure response that is received at the acoustic sensor as a function of time. The photoacoustic system may also include sensors at multiple locations. A signal representing pressure versus time or a mathematical manipulation of this signal (e.g., a scaled version thereof, etc.) may be referred to as the photoacoustic signal. The photoacoustic signal may be derived from a detected acoustic pressure signal by selecting a suitable subset of points of an acoustic pressure signal. The photoacoustic signal may also be derived using an envelope technique on the absolute values of the acoustic pressure signal. The photoacoustic signal may be used to calculate any of a number of physiological parameters, including oxygen saturation and a concentration of a blood constituent (e.g., oxyhemoglobin), at a particular spatial location. In some embodiments, photoacoustic signals from multiple spatial locations may be used to construct an image (e.g., imaging blood vessels) or a scalar field (e.g., a hemoglobin concentration field). As used herein, blood vessels are understood to include the veins, arteries, and capillaries of a subject.

In some applications, the light passed through the tissue is selected to be of one or more wavelengths that are absorbed by the constituent in an amount representative of the amount of the constituent present in the tissue. The absorption of light passed through the tissue varies in accordance with the amount of the constituent in the tissue. For example, Red and/or infrared (IR) wavelengths may be used because highly oxygenated blood will absorb relatively less Red light and more IR light than blood with a lower oxygen saturation.

Hemoglobin is understood herein to be a complex protein carried in the bloodstream of a subject that is typically involved in transporting oxygen. Hemoglobin can carry oxygen by varying the oxidation state of an iron atom within the hemoglobin protein. Hemoglobin can be found in at least two states such as oxyhemoglobin and deoxyhemoglobin. Oxyhemoglobin is understood to represent the oxygenated state of hemoglobin. Oxyhemoglobin is involved in the process of transporting oxygen molecules from, for example, the lungs to various muscles, organs and other tissues of the subject. Deoxyhemoglobin is understood to be the deoxygenated state of hemoglobin, which is occurs, for example, after a molecule of oxyhemoglobin releases oxygen for delivery to a muscle, organ, or other tissue of the subject. Methemoglobin is understood herein to be a form of oxygenated hemoglobin protein containing trivalent (i.e., ferric) iron species, as opposed to the divalent (i.e., ferrous) iron species of oxyhemoglobin.

Any suitable light sources may be used, and characteristics of the light provided by the light sources may be controlled in any suitable manner. In some embodiments, a pulsed light source may be used to provide relatively short-duration pulses (e.g., nano-second pulses) of light to the region of interest. Accordingly, the use of a pulse light source may result in a relatively broadband acoustic response (e.g., depending on the pulse duration). The use of a pulsed light source will be referred to herein as the "Time Domain Photoacoustic" (TD-PA) technique. A convenient starting point for analyzing a TD-PA signal is given by Eq. 1:

$$p(z) = \Gamma \mu_a \phi(z) \quad (1)$$

under conditions where the irradiation time is small compared to the characteristic thermal diffusion time determined by the properties of the specific tissue type. Referring to Eq. 1, p(z) is the photoacoustic signal (indicative of the maximum induced pressure rise, derived from an acoustic signal) at spatial location z indicative of acoustic pressure, $\Gamma$ is the dimensionless Grüneisen parameter of the tissue, $\mu_a$ is the effective absorption coefficient of the tissue (or constituent thereof) to the incident light, and $\phi(z)$ is the optical fluence at spatial location z. The Grüneisen parameter is a dimensionless description of thermoelastic effects, and may be illustratively formulated by Eq. 2:

$$\Gamma = \frac{\beta c_a^2}{C_P} \quad (2)$$

where $c_a$ is the speed of sound in the tissue, $\beta$ is the isobaric volume thermal expansion coefficient, and $C_p$ is the specific heat at constant pressure. In some circumstances, the optical fluence, at spatial location z (within the subject's tissue) of interest may be dependent upon the light source, the location itself (e.g., the depth), and optical properties (e.g., scattering coefficient, absorption coefficient, or other properties) along the optical path. For example, Eq. 3 provides an illustrative expression for the attenuated optical fluence at a depth z:

$$\phi(z) = \phi_0 e^{-\mu_{eff} z} \quad (3)$$

where $\phi_0$ is the optical fluence from the light source incident at the tissue surface, z is the path length (i.e., the depth into the tissue in this example), and $\mu_{eff}$ is an effective attenuation coefficient of the tissue along the path length in the tissue in this example.

In some embodiments, a more detailed expression or model may be used rather than the illustrative expression of Eq. 3. In some embodiments, the actual pressure encountered by an acoustic detector may be proportional to Eq. 1, as the focal distance and solid angle (e.g., face area) of the detector may affect the actual measured photoacoustic signal. In some embodiments, an ultrasound detector positioned relatively farther away from the region of interest, will encounter a relatively smaller acoustic pressure. For example, the peak acoustic pressure signal received at a circular area $A_d$ positioned at a distance R from the illuminated region of interest may be given by Eq. 4:

$$p_d = p(z) f(r_s, R, A_d) \quad (4)$$

where $r_s$ is the radius of the illuminated region of interest (and typically $r_s < R$), and p(z) is given by Eq. 1. In some embodiments, the detected acoustic pressure amplitude may decrease as the distance R increases (e.g., for a spherical acoustic wave).

In some embodiments, a modulated CW light source may be used to provide a photonic excitation of a tissue constituent to cause a photoacoustic response in the tissue. The CW light source may be intensity modulated at one or more characteristic frequencies. The use of a CW light source, intensity modulated at one or more frequencies, will be referred to herein as the "Frequency Domain Photoacoustic" (FD-PA) technique. Although the FD-PA technique may include using frequency domain analysis, the technique may use time domain analysis, wavelet domain analysis, or any other suitable analysis, or any combination thereof. Accordingly, the term "frequency domain" as used in "FD-PA" refers to the frequency modulation of the photonic signal, and not to the type of analysis used to process the photoacoustic response.

Under some conditions, the acoustic pressure p(R,t) at detector position R at time t, may be shown illustratively by Eq. 5:

$$p(R, t) \sim \frac{p_0(r_0, \omega)}{R} e^{-i\omega(t-\tau)} \quad (5)$$

where $r_0$ is the position of the illuminated region of interest, $\omega$ is the angular frequency of the acoustic wave (caused by modulation of the photonic signal at frequency $\omega$), R is the distance between the illuminated region of interest and the detector, and $\tau$ is the travel time delay of the wave equal to $R/c_a$, where $c_a$ is the speed of sound in the tissue. The FD-PA spectrum $p_0(r_0,\omega)$ of acoustic waves is shown illustratively by Eq. 6:

$$p_0(r_0, \omega) = \frac{\Gamma \mu_a \phi(r_0)}{2(\mu_a c_a - i\omega)} \quad (6)$$

where $\mu_a c_a$ represents a characteristic frequency (and corresponding time scale) of the tissue.

In some embodiments, a FD-PA system may temporally vary the characteristic modulation frequency of the CW light source, and accordingly the characteristic frequency of the associated acoustic response. For example, the FD-PA system may use linear frequency modulation (LFM), either increasing or decreasing with time, which is sometimes referred to as "chirp" signal modulation. Shown in Eq. 7 is an illustrative expression for a sinusoidal chirp signal r(t):

$$r(t) = \cos\left(t\left(\omega_0 + \frac{b}{2}t\right)\right) \quad (7)$$

where $\omega_0$ is a starting angular frequency, and b is the angular frequency scan rate. Any suitable range of frequencies (and corresponding angular frequencies) may be used for modulation such as, for example, 1-5 MHz, 200-800 kHz, or other suitable range, in accordance with the present disclosure. In some embodiments, signals having a characteristic frequency that changes as a nonlinear function of time may be used. Any suitable technique, or combination of techniques thereof, may be used to analyze a FD-PA signal. Two such exemplary techniques, a correlation technique and a heterodyne mixing technique, will be discussed below as illustrative examples.

In some embodiments, the correlation technique may be used to determine the travel time delay of the FD-PA signal. In some embodiments, a matched filtering technique may be used to process a photoacoustic signal. As shown in Eq. 8:

$$B_s(t-\tau) = \frac{1}{2\pi} \int_{-\infty}^{\infty} H(\omega) S(\omega) e^{i\omega t} d\omega \quad (8)$$

Fourier transforms (and inverse transforms) are used to calculate the filter output $B_s(t-T)$, in which $H(\omega)$ is the filter frequency response, $S(\omega)$ is the Fourier transform of the photoacoustic signal s(t), and T is the phase difference between the filter and signal. In some circumstances, the filter output of expression of Eq. 8 may be equivalent to an autocorrelation function. Shown in Eq. 9:

$$S(\omega) = \frac{1}{2\pi} \int_{-\infty}^{\infty} s(t) e^{-i\omega t} dt \quad (9)$$

is an expression for computing the Fourier transform $S(\omega)$ of the photoacoustic signal s(t). Shown in Eq. 10:

$$H(\omega) = S^*(\omega) e^{-i\omega \tau} \quad (10)$$

is an expression for computing the filter frequency response $H(\omega)$ based on the Fourier transform of the photoacoustic signal s(t), in which $S^*(\omega)$ is the complex conjugate of $S(\omega)$. It can be observed that the filter frequency response of Eq. 10 requires the frequency character of the photoacoustic signal be known beforehand to determine the frequency response of the filter. In some embodiments, as shown by Eq. 11:

$$B(t) = \int_{-\infty}^{\infty} r(t') s(t+t') dt' \quad (11)$$

the known modulation signal r(t) may be used for generating a cross-correlation with the photoacoustic signal. The cross-correlation output B(t) of Eq. 11 is expected to exhibit a peak at a time t equal to the acoustic signal travel time $\tau$. Assuming that the temperature response and resulting acoustic response follow the illumination modulation (e.g., are coherent), Eq. 11 may allow calculation of the time delay, depth information, or both.

In some embodiments, the heterodyne mixing technique may be used to determine the travel time delay of the FD-PA signal. The FD-PA signal, as described above, may have similar frequency character as the modulation signal (e.g., coherence), albeit shifted in time due to the travel time of the acoustic signal. For example, a chirp modulation signal, such as r(t) of Eq. 7, may be used to modulate a CW light source. Heterodyne mixing uses the trigonometric identity of the following Eq. 12:

$$\cos(A)\cos(B) = \frac{1}{2}[\cos(A-B) - \cos(A+B)] \quad (12)$$

which shows that two signals may be combined by multiplication to give periodic signals at two distinct frequencies (i.e., the sum and the difference of the original frequencies). If the result is passed through a low-pass filter to remove the higher frequency term (i.e., the sum), the resulting filtered, frequency shifted signal may be analyzed. For example, Eq. 13 shows a heterodyne signal L(t):

$$L(t) = \langle r(t)s(t) \rangle \cong \left\langle Kr(t)r\left(t - \frac{R}{c_a}\right)\right\rangle = \frac{1}{2}K\cos\left(\frac{R}{c_a}bt + \theta\right) \quad (13)$$

calculated by low-pass filtering (shown by angle brackets) the product of modulation signal r(t) and photoacoustic signal s(t). If the photoacoustic signal is assumed to be equivalent to the modulation signal, with a time lag $R/c_a$ due to travel time of the acoustic wave and amplitude scaling K, then a convenient approximation of Eq. 13 may be made, giving the rightmost expression of Eq. 13. Analysis of the rightmost expression of Eq. 13 may provide depth information, travel time, or both. For example, a fast Fourier transform (FFT) may be performed on the heterodyne signal, and the frequency associated with the highest peak may be considered equivalent to time lag $Rb/C_a$. Assuming that the frequency scan rate b and the speed of sound $c_a$ are known, the depth R may be estimated.

In a photoacoustic measurement system, a high power light source (e.g., a pulsed laser diode) may generate an acoustic pressure signal with a high signal-to-noise ratio (SNR). A high SNR may be desirable for determining physiological parameters including, for example, cardiac output. Cardiac output, as used herein, is understood to include the amount of blood pumped by the heart over a particular time interval. One clinical method of determining cardiac output includes rapidly injecting an amount of indicator dilution (e.g., saline) into a blood vessel and subsequently measuring the time-dependent change in blood concentration (i.e., indicator dilution curve) downstream from the indicator dilution injection site. A relatively fast return from the diluted state to a baseline blood concentration may indicate a high cardiac output, while a slow return may indicate low cardiac output. A photoacoustic system with high SNR may be used to accurately monitor the indicator dilution response and determine physiological parameters such as cardiac output.

A further example of a physiological parameter that a high SNR photoacoustic system may be used to determine is internal temperature. For example, in a clinical setting, the internal temperature of a patient recovering from hypothermia or undergoing cryotherapy may be desired to adjust treatment parameters. For many tissues, the Grüneisen parameter may be highly sensitive to changes in temperature, while optical absorption parameters may be relatively insensitive to temperature changes. The use of photoacoustic temperature measurements may allow for accurate, non-invasive internal temperature determination.

In some embodiments, the high signal to noise ratio provided by a pulsed laser diode may be required to eliminate background effects that may interfere with cardiac output or temperature measurements. It will be understood that high SNR photoacoustic signals may be used for any suitable photoacoustic measurement where they are available. For example, implementation of photoacoustic systems at certain light wavelengths may be limited by the availability or price of certain system components.

The 905 nm pulsed laser diode is a semiconductor laser capable of generating high SNR photoacoustic signals. Pulsed laser diodes may in some embodiments produce relatively higher peak power than comparable continuous wave laser diodes, which may result in relatively increased SNR. Physiological parameters such as cardiac output and temperature may be determined using 905 nm light. At other wavelengths, other physiological parameters such as oxygen saturation may be determined.

In some embodiments, a 905 nm pulsed laser diode and Red and IR CW laser diodes may be used in the same system to determine a combination of physiological information. Pulsed laser diodes may not be available for use at the wavelengths required for certain measurements, for example, blood oxygen saturation, due to material constraints, cost constraints, power constraints, size constraints, other suitable constraints, or any combination thereof. A pulsed laser diode may be used in a time-domain photoacoustic (TD-PA) measurement along with one or more continuous wave laser diodes used in a frequency domain photoacoustic (FD-PA) measurement. In some embodiments, measurements from two or more light sources may be used at least in part to calculate physiological parameters. In some embodiments, a photoacoustic detector may receive acoustic pressure signals generated by more than one light source. In some embodiments, the two or more light sources may be used alternatingly at the same location, simultaneously at different locations, in any other suitable manner, or any combination thereof.

In some embodiments, the photoacoustic system may include a 905 nm pulsed laser diode as a first light source and both a 600 nm CW diode laser and an 800 nm CW diode laser as a second light source. The system may detect a first acoustic pressure signal associated with the 905 nm pulsed laser diode. This acoustic pressure signal may contain information from which certain physiological parameters may be calculated about a subject. The system may detect two additional acoustic pressure signals associated with the second light source. A first additional signal may be generated by the 600 nm light and the second may be generated by the 800 nm light. The two additional signals may be used to determine the blood oxygen saturation of the subject due to the relative difference in absorbance of oxyhemoglobin and deoxyhemoglobin at 600 nm and 800 nm. The system as described in this embodiment may use the high signal to noise ratio of a pulsed laser diode to determine cardiac output, as the cardiac output measurement benefits from high illuminating power. The system as described in this embodiment may use the wide range of wavelengths available in continuous wave laser diodes to determine blood oxygen saturation, as blood oxygen saturation measurements benefit from specific wavelengths of light.

In some embodiments, the system may use a pulsed laser diode to determine a temperature or cardiac output parameter using an acoustic pressure signal corresponding to a single wavelength photonic signal. The system may use a second pulsed laser diode or continuous wave laser diode to determine a second physiological parameter requiring an acoustic pressure signal associated with more than one wavelength photonic signal. For example, the system may use two pulsed laser diodes, two continuous wave laser diodes, one pulsed laser diode and one continuous wave laser diode, one pulsed laser diode and two continuous wave laser diodes, any other suitable combination of light sources, or any combination thereof. It will be understood that the laser diodes may include non-diode lasers and other suitable light sources (e.g., LEDs). In some embodiments, more than one physiological parameter may be determined concurrently using more than one light source. In some embodiments, light sources may be located proximal to the subject. In some embodiments, one or more light sources may be coupled to the subject using fiber optic cables or other suitable light pipes.

The following description and accompanying FIGS. 1-9 provide additional details and features of some embodiments of using multiple light sources in a photoacoustic system.

FIG. 1 shows an illustrative physiological monitoring system in accordance with some embodiments of the present disclosure. System 10 may include sensor unit 12 and monitor 14. In some embodiments, sensor unit 12 may be part of a photoacoustic monitor or imaging system. Sensor unit 12 may include one or more light sources including pulsed light source 16 and continuous wave light source 17 for emitting light at one or more wavelengths into a subject's tissue, which may but need not correspond to visible light, into a subject's tissue. Pulsed light source 16 and continuous wave light source 17 may provide one or more photonic signals including any suitable electromagnetic radiation such as, for example, a radio wave, a microwave wave, an infrared wave, a visible light wave, ultraviolet wave, any other suitable light wave, or any combination thereof. Pulsed light source 16 and continuous wave light source 17 may be time modulated, frequency modulated, continuous, modulated in any other suitable way, or any combination thereof. A detector 18 may also be provided in sensor unit 12 for detecting the acoustic (e.g., ultrasound) response that travels through the subject's tissue. Any suitable physical configuration of pulsed light source 16, continuous wave light source 17, detector 18, or any combination thereof, may be used. In some embodiments, pulse light source 16, continuous wave light source 17, or both may include multiple light sources. In some embodiments, detector 18 may include one or more detectors. In some embodiments, sensor unit 12 may include multiple light sources and/or acoustic detectors, which may be spaced apart.

It will be understood that the pulsed light source 16 and continuous wave light source 17 may not be purely monochromatic. For example, light referred to herein as 700 nm may be a Gaussian, Lorentzian, other distribution, or any combination thereof, centered at 700 nm. The distribution may have a relatively sharp form, such that, for example, 90% of a light source centered at 700 nm is between 695 nm and 705 nm. The light may be generated using a substantially single color lamp such as a diode emitter, laser diode emitter, or laser. Laser light sources may have a narrower wavelength distribution than non-laser light sources. The light may be generated using a continuous or multi-peak emitting light such as a tungsten filament lamp, Xe discharge lamp, Hg discharge lamp, other suitable light source, or any combination thereof. The system may filter and condition the light using high-pass filters, low-pass filters, band-pass filters, band-stop filters, prisms, diffraction gratings, mirrors, lenses, other suitable light conditioning devices, or any combination thereof.

System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12 (e.g., a photoplethysmograph sensor). Multiple sensor units may be capable of being positioned at two or more different locations on a subject's body.

In some embodiments, system 10 may include two or more sensors forming a sensor array in lieu of either or both of the sensor units. In some embodiments, a sensor array may include multiple light sources, detectors, or both. It will be understood that any type of sensor, including any type of physiological sensor, may be used in one or more sensor units in accordance with the systems and techniques disclosed herein. It will be understood that any number of sensors measuring any number of physiological signals may be used to determine physiological information in accordance with the techniques described herein.

In some embodiments, the sensor may be wirelessly connected to monitor 14 (e.g., via wireless transceivers 38 and 24) and include its own battery or similar power source 44. In some embodiments, sensor unit 12 may draw its power from monitor 14 and be communicate with monitor 14 via a physical connection such as a wired connection (not shown). Sensor unit 12, monitor 14, or both, may be configured to calculate physiological parameters based at least in part on data relating to light emission and acoustic detection received at one or more sensor units such as sensor unit 12. For example, sensor unit 12, monitor 14, or both, may be configured to determine physiological parameters such as pulse rate, hemoglobin concentration (e.g., oxygenated, deoxygenated, total, or a combination thereof), blood oxygen saturation (e.g., arterial, venous, or both), temperature, blood pressure, cardiac output (CO), intrathoracic blood volume (ITBV), intrathoracic circulatory volume (ITCV), global end-diastolic volume (GEDV), pulmonary circulatory volume (PCV), extravascular lung water (EVLW), any other suitable hemodynamic parameters, any other suitable physiological parameters, any physiological modulations thereof, or any combination thereof. In some embodiments, some or all calculations may be performed on sensor unit 12 (i.e., using processing equipment 42) or an intermediate device and the result of the calculations may be passed to monitor 14. Further, monitor 14 may include monitor display 20 configured to display the physiological parameters or other information about the system. Sensor unit 12 may also include a sensor display 40 configured to display the physiological parameters or other information about the system and a user interface 46. In an exemplary embodiment, processing equipment 42 may be configured to operate pulsed light source 16, continuous wave light source 17, and detector 18 to generate and process acoustic signals, communicate with display sensor 40 to display values such as signal quality and power levels, receive signals from user input 46, and control wireless transceiver 38 to communicate data (e.g., acoustic output signals) with monitor 14.

In the embodiment shown, monitor 14 may also include speaker 22 to provide an audible sound that may be used in various other embodiments, such as for example, sounding an audible alarm in the event that a subject's physiological parameters are not within a predefined normal range. In another embodiment, sensor unit 12 may communicate such information to the user, e.g., using sensor display 40, an audible source such as a speaker, vibration, tactile, or any other way for communicating a status to a user, such as for example, in the event that a subject's physiological parameters are not within a predefined normal range.

In some embodiments, sensor unit 12 may be communicatively coupled to monitor 14 via a wireless system, utilizing antenna 38 of sensor unit 12 and antenna 24 of monitor 14. Antenna 38 may be external or internal to sensor unit 12, and capable of transmitting signals, receiving signals, or both transmitting and receiving signals, via amplitude modulated RF, frequency modulated RF, Bluetooth, IEEE 802.11, WiFi, WiMax, cable, satellite, infrared, any other suitable transmission scheme, or any combination thereof. Communication between the sensor unit 12 and monitor 14 may also be carried over a cable (not shown) to an input 36 of monitor 14, or to a multi-parameter physiological monitor 26 (described below). The cable may include electronic conductors (e.g., wires for transmitting electronic signals from detector 18, or a partially or fully processed signal from sensor unit 12), optical fibers (e.g., multi-mode or single-mode fibers for transmitting emitted light from pulsed light source 16 and continuous wave light source 17), any other suitable components, any suitable insulation or sheathing, or any combination thereof. Monitor 14 may include a sensor interface configured to receive physiological signals from sensor unit 12, provide signals and power to sensor unit 12, transfer data specific to the subject, general to the physiological parameter being measured, or both, or otherwise communicate with sensor unit 12. The sensor interface may include any suitable hardware, software, or both, which may allow communication between monitor 14 and sensor unit 12.

In the illustrated embodiment, system 10 includes multi-parameter physiological monitor 26. The monitor 26 may include a cathode ray tube display, a flat panel display (as shown) such as a liquid crystal display (LCD) or a plasma display, or may include any other type of monitor now known or later developed. Multi-parameter physiological monitor 26 may be configured to calculate physiological parameters and to provide a multi-parameter physiological monitor display 28 for information from sensor unit 12, monitor 14, or both, and from other medical monitoring devices or systems (not shown). For example, multi-parameter physiological monitor 26 may be configured to display an estimate of, for example, physiological parameters such as pulse rate, hemoglobin concentration (e.g., oxygenated, deoxygenated, total, or a combination thereof), blood oxygen saturation (e.g., arterial, venous, or both), temperature, blood pressure, cardiac output (CO), intrathoracic blood volume (ITBV), intrathoracic circulatory volume (ITCV), global end-diastolic volume (GEDV), pulmonary circulatory volume (PCV), extravascular lung water (EVLW), any other suitable hemodynamic parameters, any other suitable physiological parameters, any physiological modulations thereof, or any combination thereof, generated by sensor unit 12 or monitor 14. Multi-parameter physiological monitor 26 may include a speaker 30.

Monitor 14 may be communicatively coupled to multi-parameter physiological monitor 26 via a cable 32 or 34 that is coupled to a sensor input port or a digital communications port, respectively and/or may communicate wirelessly (not shown). The multi-parameter physiological monitor 26 may also be communicatively coupled to sensor unit 12 with or without the presence of monitor 14. Sensor unit 12 may be coupled to the multi-parameter physiological monitor 26 by a wireless connection using wireless transceiver 38 and a transceiver (not shown) on multi-parameter physiological monitor 26, or by a cable (not shown). In addition, sensor unit 12, monitor 14, or multi-parameter physiological monitor 26 may be coupled to a network to enable the sharing of information with servers or other workstations (not shown). In some embodiments this network may be a local area network, which may be further coupled through the internet or other wide area network for remote monitoring. Sensor unit 12, monitor 14 and multi-parameter physiological monitor 26 may be powered by a battery (not shown) or by a conventional power source such as a wall outlet.

Calibration device 80, which may be powered by monitor 14, a battery, or by a conventional power source such as a wall outlet, may include any suitable calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Figure 2:
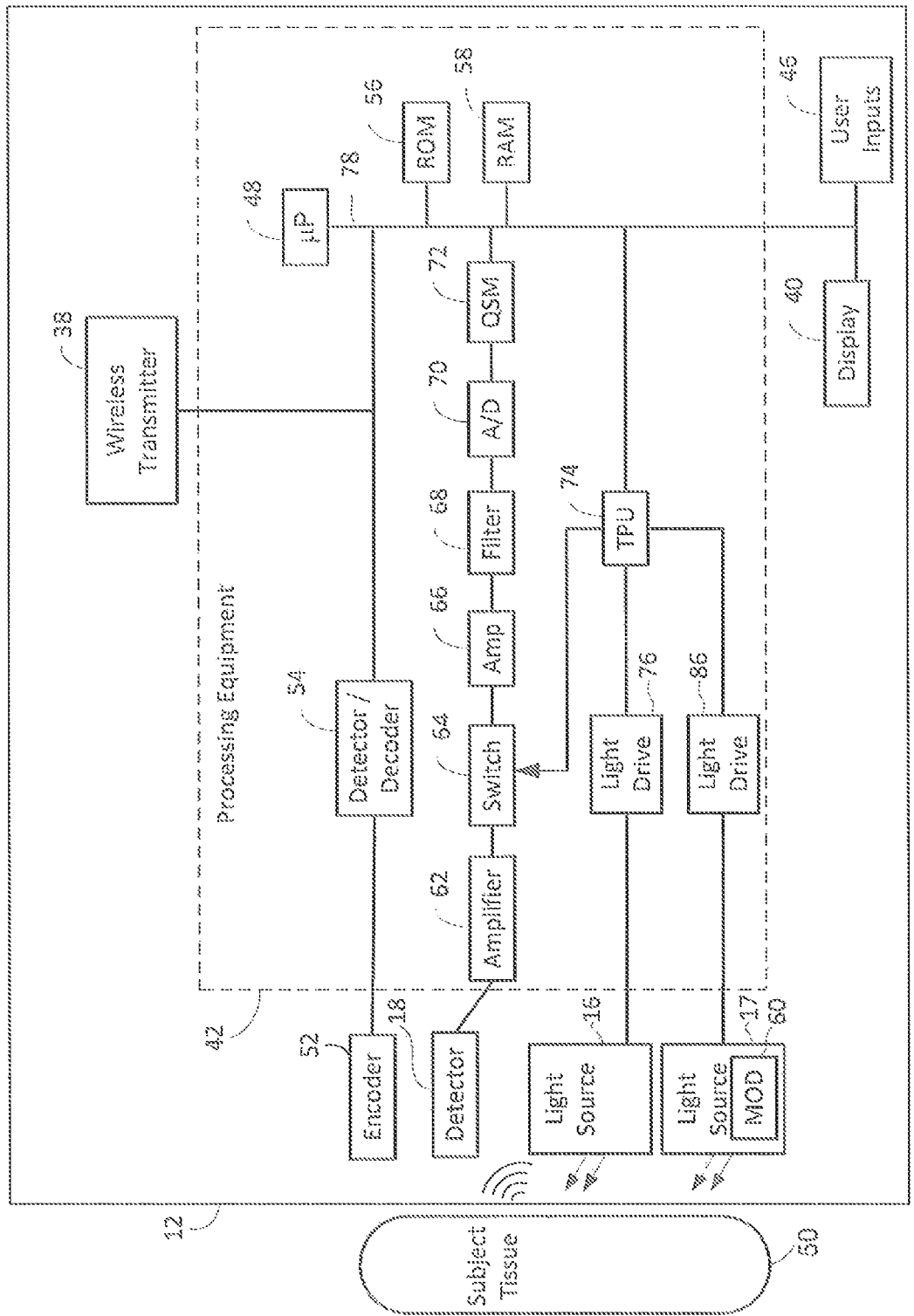
FIG. 2 is a block diagram of an illustrative sensor unit of the physiological monitoring system of FIG. 1, which may be coupled to a subject in accordance with some embodiments of the present disclosure.

FIG. 2 is a block diagram of an illustrative sensor unit 12 of physiological monitoring system 10 of FIG. 1, which may be coupled to a subject 50 in accordance with some embodiments of the present disclosure. Although in certain embodiments sensor unit 12 may include the components depicted in FIG. 2, it will be understood that some components may be located external to sensor unit 12, e.g., certain aspects of processing circuitry 42.

Sensor unit 12 may include pulsed light source 16 and continuous wave light source 17, detector 18, and encoder 52. In some embodiments, pulsed light source 16 may be configured to emit one or more wavelengths of light (e.g., visible, infrared) into a subject's tissue 50. Hence, light source 16 may provide red light, IR light, any other suitable light, or any combination thereof, that may be used to calculate the subject's physiological parameters. In some embodiments, the red wavelength may be between about 600 nm and about 700 nm, and the IR wavelength may be between about 800 nm and about 1000 nm. In embodiments where a sensor array is used in place of a single sensor, each sensor may be configured to provide light of a single wavelength. For example, a first sensor may emit only a Red light while a second may emit only an IR light. In a further example, the wavelengths of light used may be selected based on the specific location of the sensor.

In some embodiments, pulsed light source 16 may include one or more pulsed laser diodes, one or more pulsed gas laser, one or more pulsed solid state laser, one or more other suitable pulsed light sources, or any combination thereof. For example, pulsed light source light source 16 may include a pulsed laser diode (e.g., having an emission wavelength centered at about 905 nm), a continuous wave red laser diode, a continuous wave infrared laser diode, or a combination thereof.

In some embodiments, continuous wave light source 17 may include one or more continuous wave laser diodes, one or more continuous wave gas lasers, one or more continuous wave solid state lasers, one or more other suitable continuous wave light sources, or any combination thereof. For example, continuous wave light source 17 may include a continuous wave laser diode with emission wavelength centered at about 600 nm and a continuous wave laser diode with emission wavelength centered at about 800 nm.

It will be understood that the system may include any suitable number of pulsed light sources, continuous wave light sources, or any combination thereof. The light sources may be of any suitable wavelength or wavelengths. For example, the system may include one pulsed light source and no continuous wave light source. In another example, the system may include one pulsed light source and one or more continuous wave light sources. In another example, the system may include two continuous wave light sources. In some embodiments, light sources may be located at more than one location.

It will be understood that, as used herein, the term "light" may refer to energy produced by electromagnetic radiation sources. Light may be of any suitable wavelength and intensity, and modulations thereof, in any suitable shape and direction. Detector 18 may be chosen to be specifically sensitive to the acoustic response of the subject's tissue arising from use of pulsed light source 16, continuous wave light source 17, or any combination thereof. It will also be understood that, as used herein, the "acoustic response" shall refer to pressure and changes thereof caused by a thermal response (e.g., expansion and contraction) of tissue to light absorption by the tissue or constituent thereof.

In some embodiments, detector 18 may be configured to detect the acoustic response of tissue to the photonic excitation caused by the light source. In some embodiments, detector 18 may be a piezoelectric transducer which may detect force and pressure and output an electrical signal via the piezoelectric effect. In some embodiments, detector 18 may be a Faby-Pérot interferometer, or etalon. For example, a thin film (e.g., composed of a polymer) may be irradiated with reference light, which may be internally reflected by the film. Pressure fluctuations may modulate the film thickness, thus causing changes in the reference light reflection which may be measured and correlated with the acoustic pressure. In some embodiments, detector 18 may be configured or otherwise tuned to detect acoustic response in a particular frequency range. Detector 18 may convert the acoustic pressure signal into an electrical signal (e.g., using a piezoelectric material, photodetector of a Faby-Pérot interferometer, or other suitable device). After converting the received acoustic pressure signal to an electrical optical, and/or wireless signal, detector 18 may send the signal to processing equipment 42, where physiological parameters may be calculated based on the photoacoustic activity within the subject's tissue 50. The signal outputted from detector 18 and/or a pre-processed signal derived thereof, will be referred to herein as a photoacoustic signal.

In some embodiments, encoder 52 may contain information about sensor unit 12, such as what type of sensor it is (e.g., where the sensor is intended to be placed on a subject), the wavelength(s) of light emitted by pulsed light source 16, continuous wave light source 17, or any combination thereof, the intensity of light emitted by pulsed light source 16, continuous wave light source 17, or any combination thereof (e.g., output wattage or Joules), the mode of pulsed light source 16, continuous wave light source 17, or any combination thereof (e.g., pulsed versus CW), any other suitable information, or any combination thereof. This information may be used by processing equipment 42 to select appropriate algorithms, lookup tables, and/or calibration coefficients stored in processing equipment 42 for calculating the subject's physiological parameters.

Encoder 52 may contain information specific to subject's tissue 50, such as, for example, the subject's age, weight, and diagnosis. This information about a subject's characteristics may allow processing equipment 42 to determine, for example, subject-specific threshold ranges in which the subject's physiological parameter measurements should fall and to enable or disable additional physiological parameter algorithms. Encoder 52 may, for instance, be a coded resistor that stores values corresponding to the type of sensor unit 12 or the type of each sensor in the sensor array, the wavelengths of light emitted by pulsed light source 16, continuous wave light source 17, or any combination thereof on each sensor of the sensor array, and/or the subject's characteristics. In some embodiments, encoder 52 may include a memory on which one or more of the following information may be stored for communication to processing equipment 42: the type of the sensor unit 12; the wavelengths of light emitted by pulsed light source 16, continuous wave light source 17, or any combination thereof; the particular acoustic range that each sensor in the sensor array is monitoring; the particular acoustic spectral characteristics of a detector; a signal threshold for each sensor in the sensor array; any other suitable information; or any combination thereof.

In some embodiments, signals from detector 18 and encoder 52 may be transmitted to processing equipment 42. In the embodiment shown, processing equipment 42 may include a general-purpose microprocessor 48 connected to an internal bus 78. Microprocessor 48 may be adapted to execute software, which may include an operating system and one or more applications, as part of performing the functions described herein. Also connected to bus 78 may be a read-only memory (ROM) 56, a random access memory (RAM) 58, user inputs 46, sensor display 40, and speaker 22 of FIG. 1.

RAM 58 and ROM 56 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules, or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, time processing unit (TPU) 74 may provide timing control signals to light drive circuitry 76, which may control the activation of pulsed light source 16, and to light drive circuitry 86 which may drive continuous wave light source 17. For example, TPU 74 may control pulse timing (e.g., pulse duration and inter-pulse interval) for TD-PA monitoring system. TPU 74 may also control the gating-in of signals from detector 18 through amplifier 62 and switching circuit 64. It will be understood that in some embodiments, pulsed light source 16, continuous wave light source 17, or any combination thereof, may be coupled to TPU 74 without light drive circuitry 76 or light drive circuitry 86, may be coupled to bus 78, may be coupled to processing equipment and controlled by any other suitable technique, or any combination thereof.

The received signal from detector 18 may be passed through amplifier 66, low pass filter 68, and analog-to-digital converter 70. The digital data may then be stored in a queued serial module (QSM) 72 (or buffer) for later downloading to RAM 58 as QSM 72 is filled. In some embodiments, there may be multiple separate parallel paths having components equivalent to amplifier 62, filter 68, and/or analog-to-digital converter 70 for multiple light wavelengths or spectra received. Any suitable combination of components (e.g., microprocessor 48, RAM 58, analog-to-digital converter 70, any other suitable component shown or not shown in FIG. 2) coupled by bus 78 or otherwise coupled (e.g., via an external bus), may be referred to as "processing equipment."

In the embodiment shown, continuous wave light source 17 may include modulator 60, in order to, for example, perform FD-PA analysis. Modulator 60 may be configured to provide intensity modulation, spatial modulation, any other suitable optical signal modulations, or any combination thereof. For example, continuous wave light source 17 may be a continuous wave laser diode, and modulator 60 may provide intensity modulation of the CW light source such as using a linear sweep modulation. In some embodiments, modulator 60 may be included in light drive 60, or other suitable components of physiological monitoring system 10, or any combination thereof.

In some embodiments, the circuitry required to enable pulsed mode operation of pulsed light source 16 may be included in light drive 76, in circuitry included in pulsed light source 16, in any other suitable location, or any combination thereof. For example, circuitry to enable pulsed mode operation may include storage capacitors, switches, timer circuits, any other suitable components, or any combination thereof. In some embodiments, a modulator (not shown) may be included in pulsed light source 16 to enable time or frequency modulation of the photonic signal.

In some embodiments, microprocessor 48 may determine the subject's physiological parameters, such as pulse rate, hemoglobin concentration (e.g., oxygenated, deoxygenated, total, or a combination thereof), blood oxygen saturation (e.g., arterial, venous, or both), temperature, blood pressure, cardiac output (CO), intrathoracic blood volume (ITBV), intrathoracic circulatory volume (ITCV), global end-diastolic volume (GEDV), pulmonary circulatory volume (PCV), extravascular lung water (EVLW), any other suitable hemodynamic parameters, any other suitable physiological parameters, any physiological modulations thereof, or any combination thereof, using various algorithms and/or look-up tables based on the value of the received signals and/or data corresponding to the acoustic response received by detector 18. Signals corresponding to information about subject 50, and particularly about the acoustic signals emanating from a subject's tissue over time, may be transmitted from encoder 52 to decoder 54. These signals may include, for example, encoded information relating to subject characteristics. Decoder 54 may translate these signals to enable the microprocessor to determine the thresholds based at least in part on algorithms or look-up tables stored in ROM 56. In some embodiments, user inputs 46 may be used enter information, select one or more options, provide a response, input settings, any other suitable inputting function, or any combination thereof. User inputs 46 may be used to enter information about the subject, such as, for example, age, weight, height, diagnosis, medications, treatments, and so forth. In some embodiments, sensor display 40 may exhibit a list of values, which may generally apply to the subject, such as, for example, age ranges or medication families, which the user may select using user inputs 46.

The acoustic signal attenuated by the tissue of subject 50 can be degraded by noise, among other sources. Movement of the subject may also introduce noise and affect the signal. For example, the contact between the detector and the skin, or the light source and the skin, can be temporarily disrupted when movement causes either to move away from the skin. Another potential source of noise is electromagnetic coupling from other electronic instruments.

Noise (e.g., from subject movement) can degrade a sensor signal relied upon by a care provider, without the care provider's awareness. This is especially true if the monitoring of the subject is remote, the motion is too small to be observed, or the care provider is watching the instrument or other parts of the subject, and not the sensor site. Processing sensor signals may involve operations that reduce the amount of noise present in the signals, control the amount of noise present in the signal, or otherwise identify noise components in order to prevent them from affecting measurements of physiological parameters derived from the sensor signals.

Figure 3:
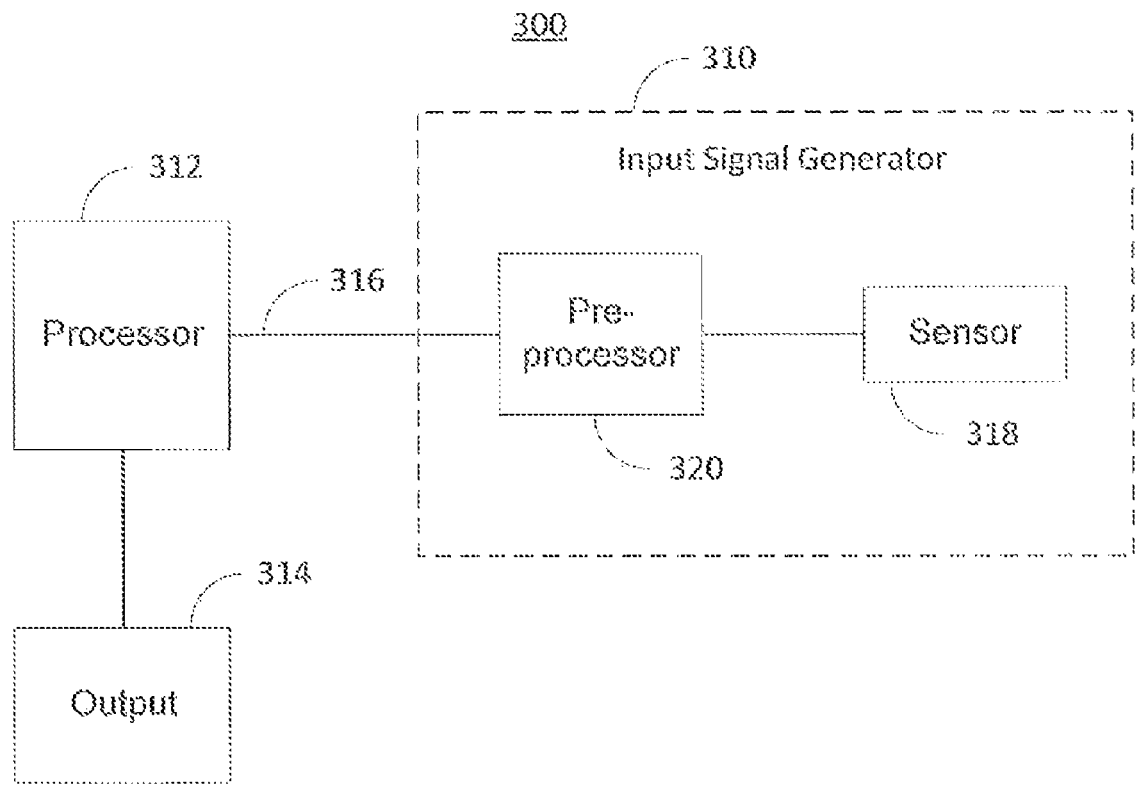
FIG. 3 is a block diagram of an illustrative signal processing system in accordance with some embodiments of the present disclosure.

FIG. 3 is a block diagram of an illustrative signal processing system in accordance with some embodiments of the present disclosure. Signal processing system 300 may implement the signal processing techniques described herein. In some embodiments, signal processing system 300 may be included in a physiological monitoring system (e.g., physiological monitoring system 10 of FIGS. 1-2). In the illustrated embodiment, input signal generator 310 generates an input signal 316. As illustrated, input signal generator 310 may include pre-processor 320 coupled to sensor 318, which may provide input signal 316. In some embodiments, pre-processor 320 may be a photoacoustic module and input signal 316 may be a photoacoustic signal. In some embodiments, pre-processor 320 may be any suitable signal processing device and input signal 316 may include one or more photoacoustic signals and one or more other physiological signals, such as a photoplethysmograph signal. The one or more photoacoustic signals may be generated by one or more light sources. For example, input signal 316 may include a photoacoustic signal associated with a continuous wave light source and a photoacoustic signal associated with a pulsed light source. It will be understood that input signal generator 310 may include any suitable signal source, signal generating data, signal generating equipment, or any combination thereof to produce input signal 316. Input signal 316 may be a single signal, or may be multiple signals transmitted over a single pathway or multiple pathways.

Pre-processor 320 may apply one or more signal processing operations to the signal generated by sensor 318. For example, pre-processor 320 may apply a pre-determined set of processing operations to the signal provided by sensor 318 to produce input signal 316 that can be appropriately interpreted by processor 312, such as performing A/D conversion. In some embodiments, A/D conversion may be performed by processor 312. Pre-processor 320 may also perform any of the following operations on the signal provided by sensor 318: reshaping the signal for transmission, multiplexing the signal, modulating the signal onto carrier signals, compressing the signal, encoding the signal, and filtering the signal.

In some embodiments, input signal 316 may be coupled to processor 312. Processor 312 may be any suitable software, firmware, hardware, or combination thereof for processing input signal 316. For example, processor 312 may include one or more hardware processors (e.g., integrated circuits), one or more software modules, and computer-readable media such as memory, firmware, or any combination thereof. Processor 312 may, for example, be a computer or may be one or more chips (i.e., integrated circuits). Processor 312 may, for example, include an assembly of analog electronic components. Processor 312 may calculate physiological information. For example, processor 312 may perform time domain calculations, spectral domain calculations, time-spectral transformations (e.g., fast Fourier transforms, inverse fast Fourier transforms), any other suitable calculations, or any combination thereof. Processor 312 may perform any suitable signal processing of input signal 316 to filter input signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the subject. Additional input signals may be used by processor 312 in any of the calculations or operations it performs in accordance with processing system 300.

In some embodiments, all or some of pre-processor 320, processor 312, or both, may be referred to collectively as processing equipment. For example, processing equipment may be configured to amplify, filter, sample and digitize input signal 316 (e.g., using an analog to digital converter), and calculate physiological information from the digitized signal.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. In some embodiments, processor 312 may store physiological measurements or previously received data from signal 316 in a memory device for later retrieval. In some embodiments, processor 312 may store calculated values, such as such as pulse rate, hemoglobin concentration (e.g., oxygenated, deoxygenated, total, or a combination thereof), blood oxygen saturation (e.g., arterial, venous, or both), temperature, blood pressure, cardiac output (CO), intrathoracic blood volume (ITBV), intrathoracic circulatory volume (ITCV), global end-diastolic volume (GEDV), pulmonary circulatory volume (PCV), extravascular lung water (EVLW), any other suitable hemodynamic parameters, any other suitable physiological parameters, any physiological modulations thereof, or any combination thereof, in a memory device for later retrieval.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIG. 1), in which, for example, input signal generator 310 may be implemented as part of sensor unit 12 (FIGS. 1 and 2), monitor 14 (FIG. 1), and processing equipment 42 (FIG. 2), and processor 312 may be implemented as part of monitor 14 (FIG. 1) and processing equipment 42 (FIG. 2). In some embodiments, portions of system 300 may be configured to be portable. For example, all or part of system 300 may be embedded in a small, compact object carried with or attached to the subject (e.g., a watch, other piece of jewelry, or a smart phone). In some embodiments, a wireless transceiver (not shown) may also be included in system 300 to enable wireless communication with other components of system 10 (FIG. 1). As such, system 10 (FIG. 1) may be part of a fully portable and continuous physiological monitoring solution. In some embodiments, a wireless transceiver (not shown) may also be included in system 300 to enable wireless communication with other components of system 10. For example, pre-processor 320 may output signal 316 (e.g., which may be a pre-processed photoacoustic signal) over BLUETOOTH, IEEE 802.11, WiFi, WiMax, cable, satellite, Infrared, any other suitable transmission scheme, or any combination thereof. In some embodiments, a wireless transmission scheme may be used between any communicating components of system 300.

It will also be understood that while some of the equations referenced herein are continuous functions, the processing equipment may be configured to use digital or discrete forms of the equations in processing the acquired photoacoustic signals.

Figure 4:
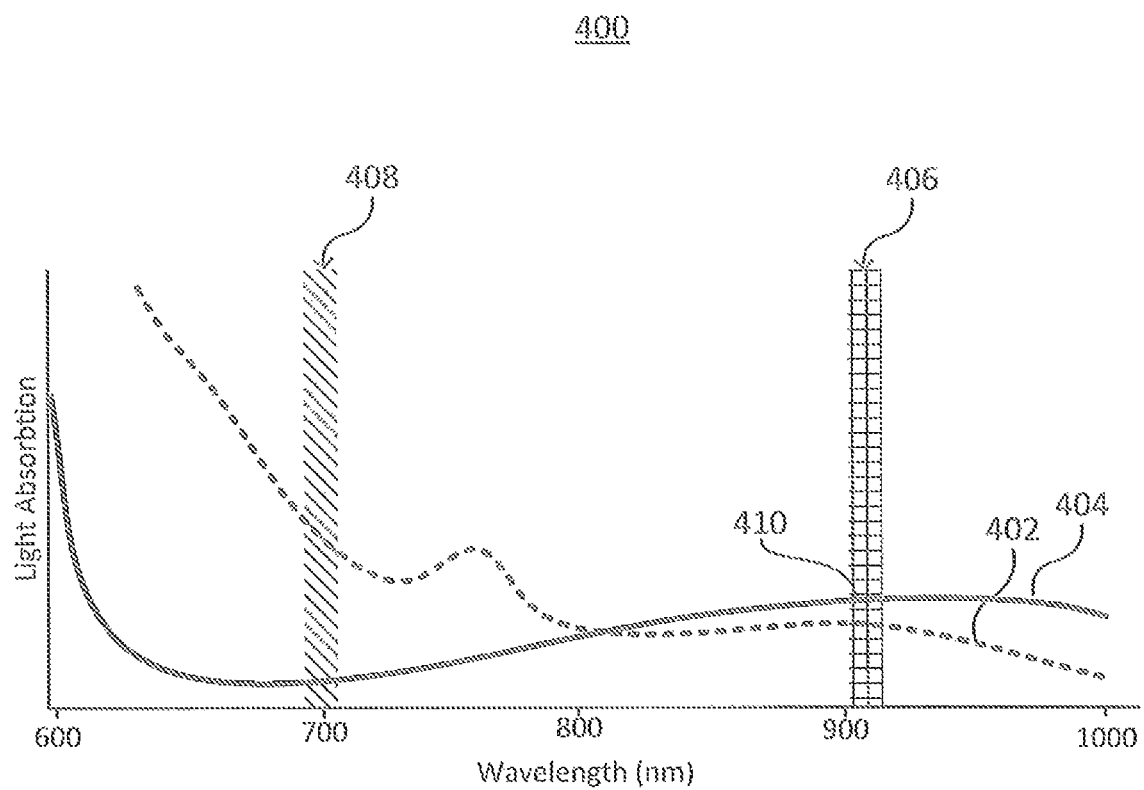
FIG. 4 is an illustrative plot of blood solute light absorption at a range of wavelengths in accordance with some embodiments of the present disclosure.

FIG. 4 is an illustrative plot 400 of blood solute light absorption at a range of wavelengths in accordance with some embodiments of the present disclosure. The abscissa of plot 400 is shown in units of wavelength of light. The ordinate of plot 400 is shown in units of light absorption in relative units of intensity. Curve 402 may represent, for example, the light absorption of deoxyhemoglobin at a range of wavelengths. Curve 404 may represent, for example, the light absorption of oxyhemoglobin at a range of wavelengths. Plot 400 shows that at different wavelengths, the relative light absorption of deoxyhemoglobin may be higher than, lower than, or the same as the light absorption of oxyhemoglobin. For example, at wavelengths near 700 nm, indicated by shaded region 408, the light absorption of deoxyhemoglobin (indicated by curve 402) is relatively higher than the light absorption of oxyhemoglobin (indicated by curve 404). In another example, at wavelengths near 905 nm, indicated by shaded region 406, the light absorption of oxyhemoglobin is relatively higher than the light absorption of deoxyhemoglobin. The relative difference between the light absorption of oxyhemoglobin and deoxyhemoglobin may be relatively more in shaded region 408 and relatively less in shaded region 408.

It will be understood that curve 402 and curve 404 of plot 400 are merely illustrative and the photoacoustic system may use any suitable light absorption properties of any suitable illuminated tissues or structures. It will also be understood that the curves illustrated in plot 400 may differ between subjects and between target areas. In some embodiments, the system may use multiple wavelengths of light with relatively different light absorption properties of blood solutes at those wavelengths (e.g., shaded region 408 and shaded region 406) to determine, for example, relative concentrations of a particular blood solute. In some embodiments, the system may use a single wavelength of light to determine, for example, temperature or cardiac output. In some embodiments, multiple measurements may be used in combination to determine physiological parameters. For example, information from a photoacoustic measurement using a first wavelength pulsed laser diode and a photoacoustic measurement using a second wavelength continuous wave laser diode may be combined to determine blood oxygen saturation or hemoglobin concentration. In some embodiments, measurements at an isobestic point (i.e., where the absorption of oxyhemoglobin and deoxyhemoglobin are equal) may be used to determine a physiological parameter, for example, total hemoglobin.

Figure 5:
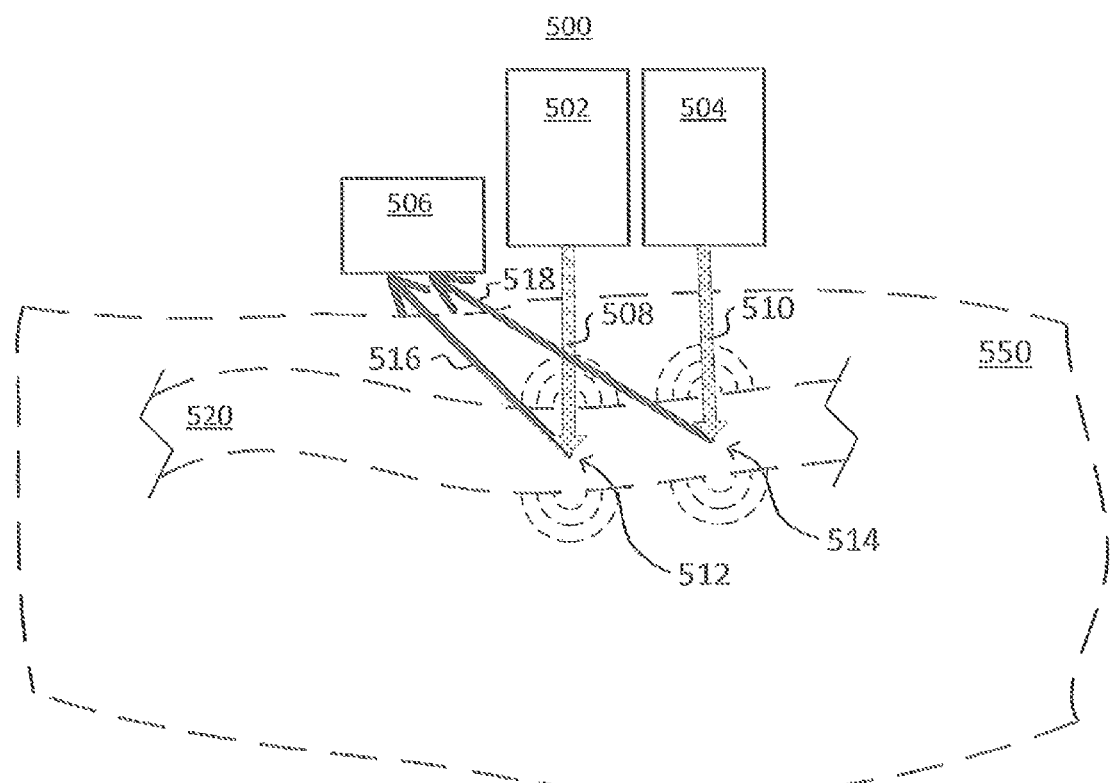
FIG. 5 is an illustrative photoacoustic arrangement in accordance with some embodiments of the present disclosure.

FIG. 5 is an illustrative photoacoustic arrangement in accordance with some embodiments of the present disclosure. The arrangement 500 may include light source 502, light source 504, and photoacoustic detector 506. Light source 502 and light source 504 may be controlled by a suitable light drive (e.g., a light drive of system 300 of FIG. 3 or system 10 of FIG. 1, although not shown in FIG. 5).

Light source 502 may include a pulsed light source (e.g., pulsed light source 16 of FIG. 1). In some embodiments, light source 502 may include a pulsed laser diode which may provide a high signal to noise ratio photoacoustic signal as compared other light sources, for example, an LED. In some embodiments, light source 502 may include a pulsed laser diode with a wavelength of 905 nm configured for time-domain photoacoustic analysis. Light source 502 may provide photonic signal 508 to subject tissue 550 including blood vessel 520. Photonic signal 508 may be attenuated along its path length by subject tissue 550 prior to reaching target area 512 for blood vessel 520. It will be understood that photonic signal 508 may scatter in subject 550 and need not travel in a well-formed beam as illustrated. Also, photonic signal 508 may generally travel through and beyond blood vessel 520. A constituent of the blood in blood vessel 520 such as, for example, hemoglobin, may absorb at least some of photonic signal 508. Accordingly, the blood may exhibit an acoustic pressure response via the photoacoustic effect, which may act on the surrounding tissues of blood vessels 520.

Light source 504 may include a light source (e.g., continuous wave light source 17 of FIG. 1). In some embodiments, light source 504 may include a continuous wave laser diode that that provides a modulated photonic signal. Light source 504 may include one or more individual light sources with wavelengths between 400 nm and 2000 nm. In some embodiments, light source 504 may include one or more continuous wave (CW) laser diode configured for frequency domain photoacoustic analysis. For example, light source 504 may include a laser diode operating at a red wavelength and a laser diode operating in the infrared. Light source 504 may provide photonic signal 510 to subject tissue 550 including blood vessel 520. Photonic signal 510 may be attenuated along its path length by subject tissue 550 prior to reaching target area 514 for blood vessel 520. It will be understood that photonic signal 510 may scatter in subject 550 and need not travel in a well-formed beam as illustrated. Also, photonic signal 510 may generally travel through and beyond blood vessel 520. A constituent of the blood in blood vessel 520 such as, for example, hemoglobin, may absorb at least some of photonic signal 510. Accordingly, the blood may exhibit an acoustic pressure response via the photoacoustic effect, which may act on the surrounding tissues of blood vessels 520.

Photoacoustic signal 516 may be generated near target area 512 of blood vessel 520 by photonic signal 508 and may travel through subject tissue 550 in all directions. Photoacoustic signal 518 may be generated near target area 514 of blood vessel 520 by photonic signal 510 and may travel through subject 550 in all directions. Acoustic detector 506 (i.e., a photoacoustic detector) may detect acoustic pressure signals corresponding to photoacoustic signals 516 and 518. Acoustic detector 506 may output a signal to other equipment (not shown) for further processing.

It will be understood that the arrangement shown in FIG. 5 is merely illustrative and any suitable arrangement of light sources and detectors may be used. In some embodiments, light source 502 and light source 504 may be enclosed in a single structure. In some embodiments, the photonic signals from light source 502 and light source 504 may follow substantially the same path. This may be accomplished, for example, by using suitable light guides or placing light source 502 and light source 504 in close proximity to each other. In some embodiments, the system may use more than one acoustic detector. In some embodiments, an acoustic detector may be paired with each light source in a separate structure. In some embodiments, the light sources may illuminate more than one blood vessel. In some embodiments, the light sources may be arranged to limit heating of subject 550.

Figure 6:
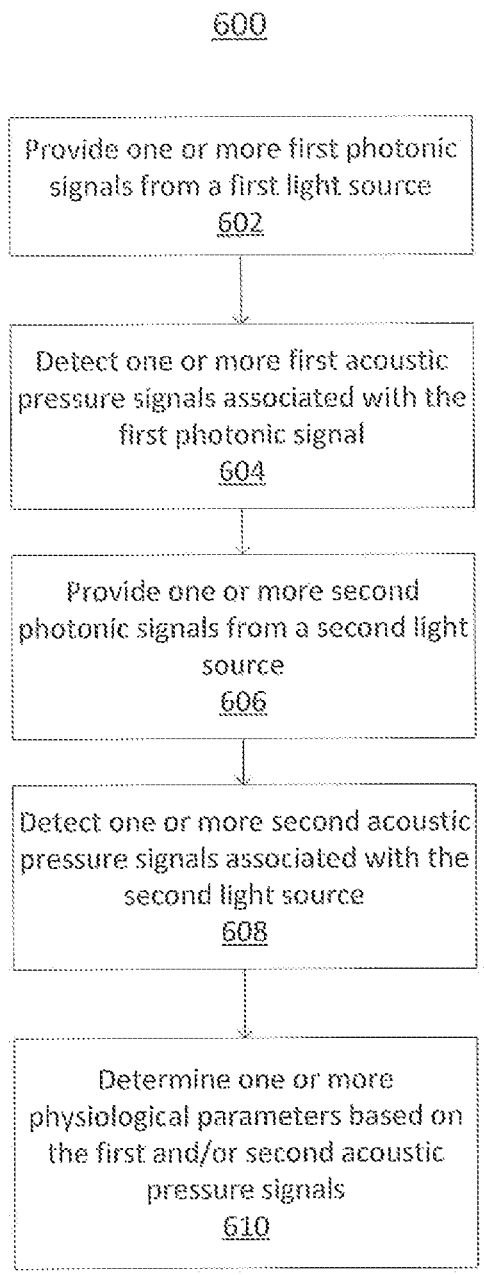
FIG. 6 is a flow diagram showing illustrative steps for determining one or more physiological parameters in accordance with some embodiments of the present disclosure.

FIG. 6 is flow diagram 600 showing illustrative steps for determining one or more physiological parameters in accordance with some embodiments of the present disclosure. In step 602, the system may provide one or more first photonic signals from a first light source. The first light source may be, for example, a pulsed laser diode operating at an emission wavelength of 905 nm. The light source may be, for example, light source 16 of FIG. 1, light source 502 of FIG. 5, any other suitable light source, or any combination thereof. The system may use particular wavelengths of light to determine physiological parameters of a subject.

In step 604, the system may detect a first acoustic pressure signal generated in the tissue of a subject in response to the one or more first photonic signals from the first light source. The first acoustic pressure signal may be detected using an acoustic detector. The acoustic detector may, for example, be detector 18 of FIG. 1. The first acoustic pressure signal may include a pressure signal generated as a result of the photoacoustic effect, as described above. The acoustic detector may include an ultrasonic detector or microphone capable of detecting an acoustic pressure signal. The corresponding photoacoustic signal may include one or more components corresponding to the one or more photonic signals. It will be understood that components may also be referred to herein as separate signals. In some embodiments, the photoacoustic signal may be a processed version of the acoustic detector signal. For example, the photoacoustic signal may be derived based on an envelope detection performed on the acoustic detector signal.

In step 606, the system may provide one or more second photonic signals from a second light source. The second light source may include light source 17 of FIG. 1, light source 504 of FIG. 5, any other suitable light source, or any combination thereof. In some embodiments, the second light source may be at least one continuous wave laser diodes. For example, the second light source may be a laser diode emitting light at about 600 nm and a laser diode emitting light at about 800 nm. In an embodiment where the second light source includes more than emitter, the individual emitters may be operated alternatingly, simultaneously, concurrently, in any other suitable arrangement, or any combination thereof.

In step 608, the system may detect a second acoustic pressure signal generated in the tissue of a subject in response to the one or more second photonic signals from the second light source. In the embodiment where the second photonic signal includes light emitted from more than one emitter, the system may detect more than one pressure signal generated from the more than one emitter. For example, in an embodiment where the second light source includes a 600 nm light source and an 800 nm light source operated in a time-alternating arrangement, the photoacoustic detector may receive alternating second acoustic pressure signals associated with 600 nm light and 800 nm light.

In step 610, the system may determine one or more physiological parameters based on the one or more first acoustic pressure signals received in step 604 and the one or more second acoustic pressure signals received in step 608. In some embodiments, the system may also use lookup tables, user inputs, any other suitable information, or any combination thereof to determine physiological parameters. For example, the system may determine a physiological parameter using only information from the one or more first acoustic pressure signals associated with the first light source. In another example, the system may determine a physiological parameter using information from the one or more first acoustic pressure signals associated with the first light source and the one or more second acoustic pressure signal associated with the second light source. In some embodiments, the system may also use information obtained elsewhere in determining a physiological parameter. In some embodiments, the system may determine more than one physiological parameter using information from the one or more first and/or second acoustic pressure signals.

In some embodiments, in step 610 the system may use a single first light source (e.g., a pulsed laser diode) to determine a physiological parameter such as, for example, temperature, cardiac output, other suitable hemodynamic parameters (e.g., intrathoracic blood volume (TTBV), intrathoracic circulatory volume (ITCV), global end-diastolic volume (GEDV), pulmonary circulatory volume (PCV), and extravascular lung water (EVLW)), or any combination thereof. The high SNR available from the first light source may result in a relatively precise measurement. In some embodiments, in step 610 the system may use more than one first light source (e.g., two pulsed laser diodes at two frequencies) to determine a physiological parameters such as, for example, blood oxygen saturation (e.g., arterial, venous, or both) and hemoglobin concentration (e.g., oxygenated, deoxygenated, total, or a combination thereof). In some embodiments, in step 610, the system may use one first light source (e.g., a pulsed laser diode) and one second light source (e.g., a CW laser diode) to determine multiple parameters, for example, the temperature and the blood oxygen saturation or any combination of the foregoing physiological parameters.

It will be understood that the above described combinations of acoustic pressure signals and other sources of information are merely exemplary and that any suitable combination of information may be used to determine any number of physiological parameters. It will also be understood that the order of steps described in flow diagram 600 is merely exemplary. For example, in some embodiments, steps 602 and 604 may occur concurrently with steps 604 and 606, the steps may occur in any other suitable order, or any combination thereof. It will also be understood that the determining of physiological parameters of step 610 may occur at any appropriate point in diagram 600. It will also be understood that flow diagram 600 is a general diagram and that the system may include additional steps to determine physiological parameters.

In some embodiments, the photonic signals provided in steps 602 and 606 and the acoustic pressure signals detected in steps 604 and 608 may be repeated multiple times. For example, a measurement as described herein may be carried out 5 times at a first wavelength and 5 times at a second wavelength. The 10 measurements may take place within one cardiac pulse cycle or over several cardiac pulse cycles such that the physiological parameters remain relatively constant. In some embodiments, the system may average measurements over, for example, seconds, minutes or hours, to improve the signal-to-noise ratio, determine a baseline, to monitor changes over time, for any other suitable reason, or any combination thereof. In another example, the system may overlay photoacoustic signals generated by multiple wavelengths to compare the signals. The multiple photoacoustic signals may be aligned to account for small shifts in time, distance, other values, or any combination thereof. In some embodiments, the system may align multiple photoacoustic signals in time with respect to the emission timing of a photonic signal from the light source. In some embodiments, the system may determine and use the center of a particular peak to align multiple signals. It will be understood that the aforementioned alignment methods are provided as examples, and other methods may be employed as well. It will also be understood that any combination of the aforementioned and other methods may be employed. It will also be understood that instead of aligning the photoacoustic signals, corresponding points in the signals can be identified and analyzed.

Figure 7:
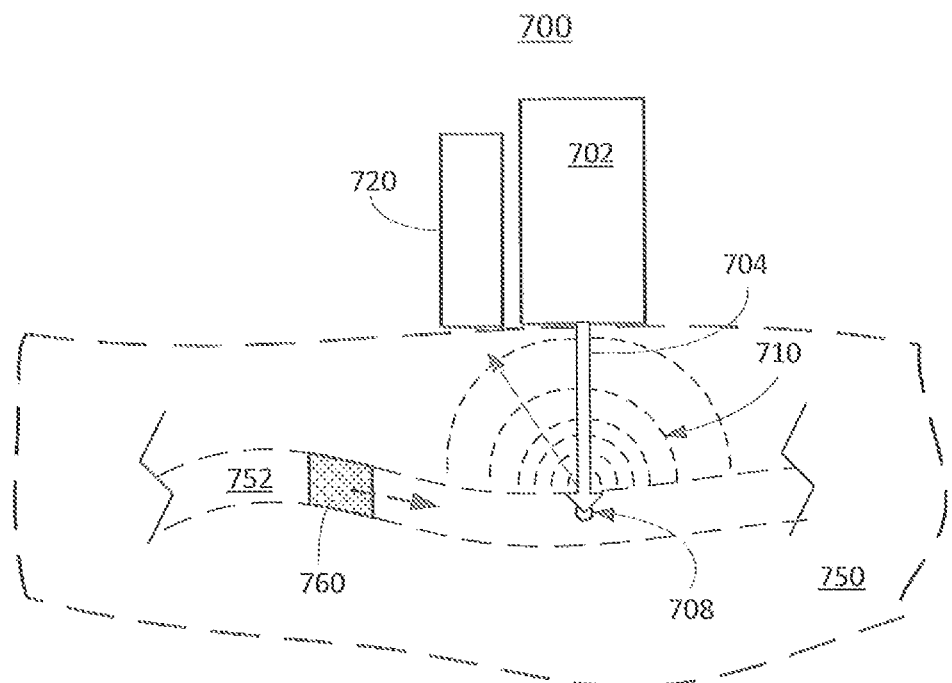
FIG. 7 shows an illustrative indicator dilution photoacoustic arrangement, in accordance with some embodiments of the present disclosure.

FIG. 7 shows an illustrative indicator dilution photoacoustic arrangement 700, in accordance with some embodiments of the present disclosure. Indicator dilution photoacoustic arrangement 700 may be used to determine, for example, cardiac output (CO), intrathoracic blood volume (ITBV), intrathoracic circulatory volume (ITCV), global end-diastolic volume (GEDV), pulmonary circulatory volume (PCV), extravascular lung water (EVLW), and/or other hemodynamic parameters as described further below.

Light source 702 may provide photonic signal 704 to subject tissue 750 including blood vessel 752. Photonic signal 704 may be attenuated along its path length by subject tissue 750 prior to reaching target area 708 for blood vessel 752. It will be understood that photonic signal 704 may scatter in subject 750 and need not travel in a well-formed beam as illustrated. Also, photonic signal 704 may generally travel through and beyond blood vessel 752. A constituent of the blood in blood vessel 752 such as, for example, hemoglobin, may absorb at least some of photonic signal 704. Accordingly, the blood may exhibit an acoustic pressure response resulting in acoustic pressure signal 710 via the photoacoustic effect, which may act on the surrounding tissues of blood vessels 752. Acoustic pressure signal 710 may be detected by acoustic detector 720. In some embodiments, changes in some properties of the blood in blood vessel 752 at site 708 may be detected by acoustic detector 720 as a change in photoacoustic signal 710. For example, a reduced hemoglobin concentration or reduced temperature at the monitoring site may cause a reduced acoustic pressure signal to be detected by acoustic detector 720. In some embodiments, bolus dose 760, which may include a suitable indicator, may be introduced to the blood of patient 750 at a suitable blood vessel site (not shown in FIG. 7). Acoustic detector 720 may detect the transient changes in the hemoglobin concentration ("hemo-dilution") and/or temperature ("thermo-dilution") at site 708 due to passage of bolus dose 760 through site 708. In some embodiments, multiple monitoring sites (not shown) may be used to detect changes in hemoglobin concentration, temperature, or both. As bolus dose 760 travels through the circulatory system of subject 750, diffusion, mixing (e.g., within a heart chamber), or both may spread the hemoglobin concentration and temperature profiles axially (i.e., in the direction of flow) and radially (i.e., normal to the direction of flow). It will be understood that hemo-dilution refers to the dilution of blood constituents caused by the bolus dose, and thermo-dilution refers to the combined effects of blood constituent dilution and temperature change, both caused by the bolus dose. In some embodiments, using a thermo-dilution indicator, a temperature change may be enhanced by hemo-dilution (e.g., when the temperature change and the dilution change both cause the photoacoustic signal to either increase or decrease), and accordingly may be detected by a system having relatively less temperature sensitivity.

It will be understood that light source 702 may correspond to light source 502 or light source 504 of FIG. 5. For example, light source 702 may include a pulsed laser diode which may provide a high signal to noise ratio photoacoustic signal. As a further example, light source 702 may include a continuous wave laser diode or any other suitable light source. It will also be understood that arrangement 700 may be included as part of system 10 of FIG. 1, sensor unit 12 of FIG. 2 or system 300 of FIG. 3.

A bolus dose of an indicator may cause the properties at a photoacoustic monitoring site to change in time as the bolus dose passes the site. Introduction of the indicator may alter one or more properties of the blood that interacts with the indicator (e.g., blood near the bolus dose). An indicator introduced as a bolus dose may be selected to have one or more properties that allow the bolus dose to be distinguished from a subject's un-dosed blood. For example, an indicator may be selected which has particular absorption properties at one or more particular wavelengths (e.g., a dye indicator such as indocyanine green dye), and the photoacoustic monitoring system may monitor the presence of the indicator by providing a photonic signal at one or more particular wavelengths and detecting an acoustic pressure signal having a dye indicator dilution response. In a further example, an indicator may be selected to dilute blood of a subject but not substantially absorb the photonic signal. The photoacoustic monitoring system may then accordingly monitor the blood (e.g., hemoglobin) rather than the indicator, to detect dilution. In a further example, an indicator having a temperature different from the temperature of the subject's un-dosed blood may be introduced into a subject's bloodstream (e.g., a "hot" or "cold" indicator, relative to the blood temperature). The photoacoustic monitoring system may then accordingly monitor the bloodstream temperature at the monitoring site, or the combined effects of hemo-dilution and thermo-dilution achieved by the bolus dose. In some embodiments, an indicator may have more than one property that may be distinguished from a subject's blood. For example, a cold dye indicator may be introduced to the subject's bloodstream, which may allow hemo-dilution and thermo-dilution effects to be detected. In some embodiments, more than one indicator may be introduced to the subject's bloodstream, each indicator having particular properties that may be unique relative to the other indicators. For example, an isotonic indicator and a hypertonic indicator may be introduced into a subject's bloodstream. In a further example, a cold isotonic indicator and a dye indicator may be introduced into a subject's bloodstream. An indicator may include saline (e.g., isotonic, hypertonic, hypotonic), dye (e.g., indocyanine), lithium, any other suitable chemical or mixture, or any combination thereof.

In some embodiments, a relatively small amount of indicator may be introduced to a subject's bloodstream. For example, a bolus dose on the order of 10 mL may be injected to act as an indicator. Accordingly, the detected response may be relatively small. For example, the temperature change caused by a thermo-dilution indicator may be less than 1° Celsius, depending on the amount of indicator used and the monitoring arrangement used.

Figure 8:
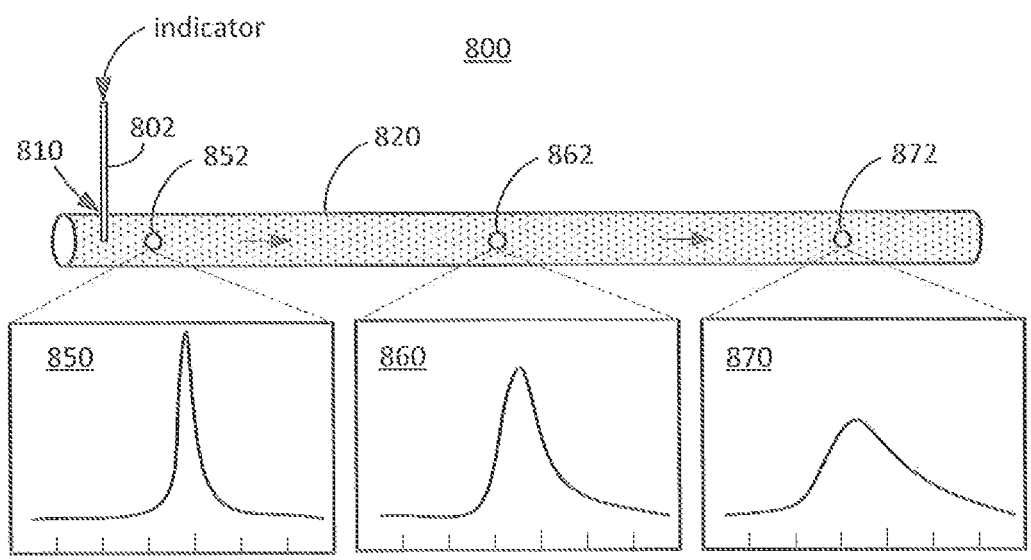
FIG. 8 shows an illustrative indicator arrangement 800, in accordance with some embodiments of the present disclosure.

FIG. 8 shows an illustrative indicator arrangement 800, in accordance with some embodiments of the present disclosure. In some embodiments, an indicator may be provided to the circulatory system of a subject to aid in determining one or more physiological parameters. For example, a saline solution may be injected into a subject's circulatory system at blood vessel site 810 using needle 802. Blood vessel site 810 may be located at any suitable portion of a subject's circulatory system such as a vein, an artery, a capillary, or other suitable location. For example, blood vessel site 810 may be a central vein of the subject. Portion 820 of the subject's circulatory system shown illustratively in FIG. 8 may include heart chambers, arteries, veins, capillaries, any other suitable parts of the circulatory system, or any combination thereof. As the indicator travels along portion 820, in the direction of the motion arrows away from the introduction site, the concentration and/or temperature profile of may change. For example, panel 850 shows an illustrative dilution curve time series as detected at site 852, relatively near site 810. Panels 860 and 870 each show illustrative time series of dilution curves at sites 862 and 872, respectively, both downstream from site 852. The dilution curve shown in panel 860 is relatively flattened in time compared to the dilution curve shown in panel 850. The dilution curve shown in panel 870 is relatively flattened in time compared to the dilution curve shown in panel 860. The flattening may be due to diffusion and mixing of the indicator with the subject's blood. The area under the time series of panels 850, 860, and 870 may be, but need not be, the same and may depend on the indicator type, travel time, site location, and other suitable variables. The phrase "dilution curve" as used herein shall refer to a time series, continuous or discrete, indicative of dilutive effects of an indicator on the concentration of blood constituents and/or blood temperature. For example, a dilution curve may include a time series of concentration or changes thereof of a blood constituent, an indicator, or both. In a further example, a dilution curve may include a time series of temperature, or change in temperature, of blood of the subject at a monitoring site. As the indicator is transported through the subject's vasculature, a portion of the indicator may travel through each blood vessel, proportional to the flow rate of blood in that vessel. Accordingly, the original bolus dose of indicator may "mix out" after some time, and a steady-state, or near steady-state condition may be achieved (e.g., similar to a steady-state or near steady-state condition before the bolus dose was introduced).

Figure 9:
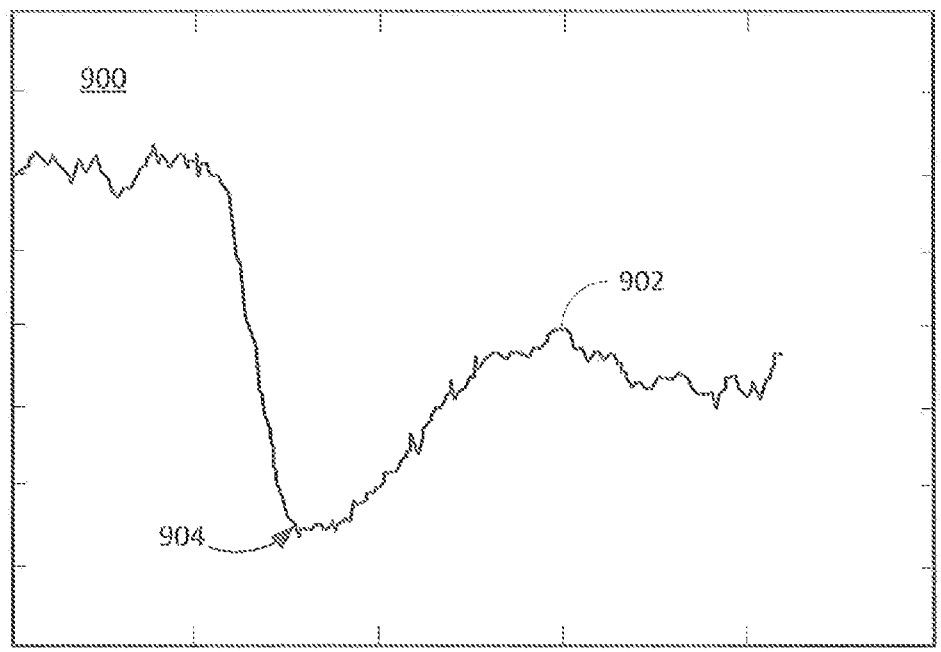
FIG. 9 shows a plot 900 of an illustrative photoacoustic signal 902, including a response to an isotonic indicator, in accordance with some embodiments of the present disclosure.

FIG. 9 shows a plot 900 of an illustrative photoacoustic signal 902, including a response corresponding to an isotonic indicator (e.g., 0.9% w/v saline), in accordance with some embodiments of the present disclosure. A light source is used to provide a photonic signal to a first site of a circulatory system, causing a photoacoustic response of constituents in the circulating blood at that site. An acoustic detector is used to detect acoustic pressure signals caused by the photonic signal at the first site, and along with processing equipment, output a corresponding photoacoustic signal. An isotonic indicator is injected as a bolus dose into the circulating blood at a second site. As the bolus dose travels past the first site, the hemoglobin concentration at the first site temporarily decreases. Trough 904 indicates the dilatory effects of the bolus dose of isotonic indicator. The processing equipment outputs a reduced photoacoustic signal caused by the reduced hemoglobin concentration. The effect of the indicator may be detected as a trough in the photoacoustic signal corresponding to the passing of the bolus dose through the first site.

In some embodiments, one or more characteristics may be derived from a response. For example, the flow rate of a particular indicator may be formulated as shown by:

$$\dot{V}C_i = \dot{N} \quad (14)$$

where $\dot{V}$ is the volumetric flow rate of blood (e.g., volume/time, assumed here to be constant in time), $C_i$ is the concentration of indicator i (e.g., mole/volume), and $\dot{N}$ is the molar flow rate of molecule i (e.g., mole/time). Defining the cardiac output CO to be equal to volumetric flow rate $\dot{V}$, the following Eq. 15 may be derived by integrating both sides of Eq. 14 in time:

$$CO = \frac{N}{A} \quad (15)$$

where cardiac output CO is proportional to the total isotonic indicator amount introduced N (e.g., moles), and A is given by:

$$A \int C_i dt \quad (16)$$

where A may be equivalent to an area bounded by the response and the steady tHb value. Under some circumstances, cardiac output may be equal to the ratio of isotonic indicator amount introduced and the area bounded by the time series and the steady tHb value, while in other circumstances the equality of Eqs. 15-16 may be replaced by the proportionality symbol ∝ (e.g., to account for density differences). Area A is an illustrative example of a characteristic derived from a response to an indicator.

In a further example, EVLW may be determined based on isotonic and hypertonic indicators, as shown by Eq. 17:

$$EVLW = CO * \Delta\tau_{MT} \quad (17)$$

where CO is the cardiac output, and $\Delta\tau_{MT}$ is the mean transit time difference between the isotonic and hypotonic indicator dilution curves. The mean transit time of an indicator dilution curve may be based on any suitable reference point of the curve. The mean transit time for a dilution curve may be calculated using Eq. 18:

$$\tau_{MT} = \tau_0 + \frac{\int C_i * (t - \tau_0) dt}{\int C_i dt} \quad (18)$$

where $\tau_0$ is the time after introduction of the indicator when the indicator is detected at the PA monitoring site, and $C_i$ is the indicator concentration.

In a further example, a vascular permeability metric vp may be defined as:

$$vp = \tau_2 - \tau_1 \quad (19)$$

where $\tau_2$ is the time corresponding to a trough (i.e., minimum, occurring after a peak) of the response to the hypertonic indicator, and $\tau_1$ is the time where the responses to the isotonic and hypertonic indicators cross. In some circumstances, vascular permeability may provide an indication and/or measure of the possibility of a capillary leak and the possibility of fluid accumulating outside of the blood vessels.

In a further example, EVLW may be determined based on an osmotic response (e.g., the transfer of water and salt between the blood and lungs due to a chemical potential difference) of the subject using an isotonic and hypertonic indicator. EVLW may be determined using the following Eq. 20, for the hypertonic indicator:

$$EVLW = \frac{\Pi_b \left( \frac{\Delta n_3}{c} - \Delta EVLW_3 \right)}{\Delta \Pi_{b,3}} \quad (20)$$

where $\Pi_b$ is the steady state osmolarity of the subject's blood (e.g., before introduction of the hypertonic indicator), $\Delta \Pi_{b,3}$ is the change in the osmolarity of subject's blood at time $\tau_3$, $\Delta n_3$ is the total amount of salt transferred from the subject's blood to the subject's lungs at time $\tau_3$, c is the concentration of solutes in the EVLW, and $\Delta EVLW_3$ is the total change in extravascular lung water at time $\tau_3$. The time $\tau_3$ is the time, referenced to zero at the beginning of the response, when the EVLW and blood have the same osmotic pressure for the hypertonic indicator.

In some embodiments, a thermo-dilution indicator may be introduced to the subject's circulatory system at a suitable location. For example, in some embodiments, a saline solution having a temperature less than that of a subject's blood may be introduced, and one or more dilution curves may be measured at one or more respective locations in the subject's vasculature. The Grüneisen parameter of the subject's blood may depend on temperature linearly according to:

$$\Gamma = mT + b \quad (21)$$

where m is a slope and b is an intercept. Accordingly, Eq. 1 may be rewritten as follows:

$$o(z, T) = \Gamma(T) \mu_a \phi(z). \quad (22)$$

Showing that as the temperature at the photoacoustic monitoring site changes, the acoustic pressure signal and a photoacoustic signal derived thereof may change accordingly. Introduction of thermo-dilution indicator may be used to determine cardiac output, ITCV, PCV, and/or GEDV, for example.

In some embodiments, cardiac output CO may be calculated using:

$$CO = K \frac{(T_{b,0} - T_{i,0}) V_i}{\int (T_{b,0} - T_b(t)) dt} \quad (23)$$

where K is a proportionality constant (e.g., including the effects of specific gravity and heat capacity of blood and/or the indicator), $T_{b,0}$ is the initial blood temperature at the time and site of injection, $T_{i,0}$ is the initial indicator temperature, $V_i$ is the volume of injected indicator, and $T_b(t)$ is the blood temperature at time t, as measured using the photoacoustic technique. Note that the moles of injected indicator may be used rather than $V_i$ in some cases, with a suitable adjustment of the proportionality constant K to include the indicator concentration (e.g., mole/volume).

In some embodiments, ITCV may be calculated using:

$$ITCV = CO * \tau_{MT} \quad (24)$$

where CO is the cardiac output, and $\tau_{MT}$ is the mean transit time of the thermo-dilution curve. The mean transit time for a thermo-dilution indicator may be calculated using:

$$\tau_{MT} = \tau_0 + \frac{\int (T_{b,0} - T_b(t)) * (t - \tau_0) dt}{\int (T_{b,0} - T_b(t)) dt} \quad (25)$$

where $\tau_0$ is the time after introduction of the indicator when the indicator is detected at the PA monitoring site, and $(T_{b,0} - T_b(t))$ is the difference in initial and instantaneous blood temperature of the thermo-dilution curve. In some embodiments, in which a thermo-dilution indicator may be used, a circulatory volume may be equivalent to a thermal volume.

In some embodiments, PCV may be calculated using:

$$PCV = CO * \tau_{DS} \quad (26)$$

where CO is the cardiac output, and $\tau_{DS}$ is the downslope time of the thermo-dilution curve. In some embodiments, the downslope time may be determined as the time interval of the linear decay of the indicator response (e.g., downslope of a peak), from about 80% of the peak value to about 20% of the peak value. In some circumstances, downslope time may provide an indication and/or measure of the washout of the indicator, which may depend on the volume which the indictor dilutes.

In some embodiments, GEDV may be calculated using:

$$GEDV = ITCV - PCV \quad (27)$$

which may be indicative of the blood volume included in the ITCV.

In some embodiments, EVLW may be calculated using:

$$EVLW = ITCV - ITBV \quad (28)$$

where ITBV may be calculated from GEDV, which may be calculated using Eq. 27. For example, ITBV may be directly proportional to GEDV, with a proportionality constant of order one (e.g., a constant of 1.25).

In some embodiments, more than one thermo-dilution indicator may be introduced to a subject. For example, two thermo-dilution indicators, at two different temperatures, may be introduced to the subject. Differences in the resulting dilution curves may provide information regarding hemo-dilution, thereto-dilution, or differences thereof.

In some embodiments, both a thermo-dilution indicator and a hemo-dilution indicator may be introduced to the subject's circulatory system at suitable locations and times. For example, in some embodiments, a saline solution having a temperature less than that of a subject's blood may be introduced, and a dye indicator such as indocyanine green dye may be introduced. Accordingly, two or more dilution curves may be measured at one or more locations in the subject's vasculature, indicative of the hemo-dilution and thermo-dilution indicators. Any of the properties that may be calculated using Eqs. 21-27 may be calculated using the thermo-dilution indicator. In some embodiments, ITBV may be calculated using the Nemo-dilution curve, as shown by:

$$ITBV=CO*\tau_{MT} \qquad (29)$$

where CO is the cardiac output (e.g., calculated using Eq. 15 or 23), and $\tau_{MT}$ is the mean transit time of the Nemo-dilution curve (e.g., calculated using Eq. 18).

In some embodiments, EVLW may be calculated from the thereto-dilution curve and hemo-dilution curve using:

$$EVLW=ITCV-ITBV \qquad (30)$$

wherein ITCV may be calculated from the thermo-dilution curve (e.g., using Eq. 24), and ITBV may be calculated from the hemo-dilution curve (e.g., using Eq. 29).

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A photoacoustic method for determining a physiological parameter, the method comprising:
   providing a pulsed photonic signal to a subject from a first light source;
   providing a modulated photonic signal to the subject from a second light source;
   detecting a first acoustic pressure signal and a second acoustic pressure signal from the subject, wherein the first acoustic pressure signal is caused by absorption of at least some of the pulsed photonic signal by the subject and the second acoustic pressure signal is caused by absorption of at least some of the modulated photonic signal by the subject;
   determining a first physiological parameter based on the first acoustic pressure signal; and
   determining a second physiological parameter, different from the first physiological parameter, based on the second acoustic pressure signal.

2. The method of claim 1, further comprising:
   determining a third physiological parameter based on both the first acoustic pressure signal and the second acoustic pressure signal.

3. The method of claim 1, wherein the first light source comprises one or more pulsed laser diodes.

4. The method of claim 1, wherein the first light source comprises one or more emitters configured to emit light with a wavelength between 900 nm and 910 nm.

5. The method of claim 1, wherein the second light source comprises one or more continuous wave laser diodes.

6. The method of claim 5, wherein the second light source comprises one or more emitters configured to emit light of two different wavelengths between 600 nm and 1200 nm.

7. The method of claim 6, wherein detecting the second acoustic pressure signal comprises detecting a first component corresponding to a first of the two different wavelengths and detecting a second component corresponding to a second of the two different wavelengths, and wherein determining the second physiological parameter comprises determining the second physiological parameter based at least in part on the first and second components.

8. The method of claim 1, wherein the first light source and the second light source are configured to emit light at different times.

9. The method of claim 1, wherein detecting the first acoustic pressure signal and the second acoustic pressure signal comprises detecting the first acoustic pressure signal and the second acoustic pressure signal using a piezoelectric ultrasound receiver array of at least one dimension.

10. The method of claim 1, wherein the first physiological parameter comprises temperature, cardiac output (CO), intrathoracic blood volume (ITBV), intrathoracic circulatory volume (ITCV), global end-diastolic volume (GEDV), pulmonary circulatory volume (PCV), extravascular lung water (EVLW), or any suitable combination thereof, and wherein the second physiological parameter comprises hemoglobin concentration, blood oxygen saturation, or any suitable combination thereof.

11. The system of claim 1, wherein the first physiological parameter is determined based on the first acoustic pressure signal and not on the second acoustic pressure signal.

12. The method of claim 1, wherein the pulse photonic signal comprises a first wavelength of light and the modulated photonic signal comprises a second wavelength of light different than the first wavelength of light.

13. A photoacoustic system for determining a physiological parameter, the system comprising:
   a first light source configured to provide a pulsed photonic signal comprising a first wavelength of light to a subject;
   a second light source configured to provide a modulated photonic signal comprising a second wavelength of light, different from the first wavelength of light, to the subject;
   at least one acoustic detector configured to detect a first acoustic pressure signal and a second acoustic pressure signal from the subject, wherein the first acoustic pressure signal is caused by absorption of at least some of the pulsed photonic signal by the subject and the second acoustic pressure signal is caused by absorption of at least some of the modulated photonic signal by the subject; and
   processing equipment communicatively coupled to the acoustic detector, the processing equipment configured to determine a first physiological parameter based on the first acoustic pressure signal and to determine a second physiological parameter, different from the first physiological parameter, based on the second acoustic pressure signal.

14. The system of claim 13, wherein the processing equipment is further configured to:
   determine a third physiological parameter using both the first acoustic pressure signal and the second acoustic pressure signal.

15. The system of claim 13, wherein the first light source comprises one or more pulsed laser diodes.

16. The system of claim 13, wherein the first light source comprises one or more emitters configured to emit light at the first wavelength and wherein the first wavelength is between 900 nm and 910 nm.

17. The system of claim 13, wherein the second light source comprises one or more continuous wave laser diodes.

18. The system of claim 17, wherein the second light source comprises one or more emitters and wherein the modulated photonic signal comprises light of a third wavelength different from the second wavelength, and wherein the second and the third wavelengths are between 600 nm and 1200 nm.

19. The system of claim 18, wherein the second acoustic pressure signal comprises a first component corresponding to the second wavelength and a second component corresponding to the third wavelength, and wherein the processing equipment is further configured to determine the second physiological parameter based on the first and second components.

20. The system of claim 13, wherein the first light source and the second light source are configured to emit light at different times.

21. The system of claim 13, wherein the at least one photoacoustic detector comprises a piezoelectric ultrasound receiver array of at least one dimension.

22. The system of claim 13, wherein the first physiological parameter comprises temperature, cardiac output (CO), intrathoracic blood volume (ITBV), intrathoracic circulatory volume (ITCV), global end-diastolic volume (GEDV), pulmonary circulatory volume (PCV), extravascular lung water (EVLW), or any suitable combination thereof, and wherein the second physiological parameter comprises hemoglobin concentration, blood oxygen saturation, or any suitable combination thereof.

23. The system of claim 13, wherein the first light source, the second light source, and the at least one acoustic detector are disposed within a housing configured to be positioned on a tissue of the subject.

\* \* \* \* \*